United States Patent
Witherspoon et al.

(10) Patent No.: US 11,986,413 B2
(45) Date of Patent: May 21, 2024

(54) FLEXGRIP

(71) Applicant: SRI International, Menlo Park, CA (US)

(72) Inventors: Katherine Goss Witherspoon, San Francisco, CA (US); Alexander Steele Kernbaum, Sunnyvale, CA (US)

(73) Assignee: SRI International, Menlo Park, CA (US)

( * ) Notice: Subject to any disclaimer, the term of this patent is extended or adjusted under 35 U.S.C. 154(b) by 1158 days.

(21) Appl. No.: 15/552,979

(22) PCT Filed: Feb. 25, 2016

(86) PCT No.: PCT/US2016/019565
§ 371 (c)(1),
(2) Date: Aug. 23, 2017

(87) PCT Pub. No.: WO2016/138264
PCT Pub. Date: Sep. 1, 2016

(65) Prior Publication Data
US 2018/0049903 A1 Feb. 22, 2018

Related U.S. Application Data

(60) Provisional application No. 62/120,794, filed on Feb. 25, 2015.

(51) Int. Cl.
*A61F 5/01* (2006.01)
*A61F 5/30* (2006.01)
(Continued)

(52) U.S. Cl.
CPC ............... *A61F 5/01* (2013.01); *A61F 5/30* (2013.01); *A61F 5/37* (2013.01); *A61H 1/02* (2013.01);
(Continued)

(58) Field of Classification Search
CPC ........ A61F 5/37; A61F 5/0111; A61F 5/0113; A61F 13/085; A61F 5/01; A61F 5/02;
(Continued)

(56) References Cited

U.S. PATENT DOCUMENTS 5,203,754 A 4/1993 Maclean
5,716,307 A 2/1998 Vadher
(Continued)

FOREIGN PATENT DOCUMENTS

JP 3043589 U 9/1997
JP 2002-125718 A 5/2002
(Continued)

OTHER PUBLICATIONS

The International Search Report (ISR) for PCT/US2016/019565 dated Jul. 4, 2016, pp. 1-3.
(Continued)

*Primary Examiner* — Michelle J Lee
*Assistant Examiner* — Robin Han
(74) *Attorney, Agent, or Firm* — MCDONNELL BOEHNEN HULBERT & BERGHOFF LLP

(57) ABSTRACT

A variety of flexible body harnesses are provided to distribute loads comfortably and evenly across one or more segments of the human body. The trajectories of load-bearing straps of the provided body harnesses apply shear to underlying portions of skin of a body segment evenly across the length of the load-bearing straps. Such trajectories can approximate catenary curves as the straps encircle the body segment. The trajectories of such straps around a body segment are maintained by attaching the straps to an underlayer, by incorporating the straps into a flexible material, and/or by weaving further straps around the load-bearing straps to maintain their relative location and/or curvature. Such body harnesses can be provided as part of assistive,
(Continued)

rehabilitative, prosthetic, or strength-enhancing systems configured to apply forces to the body via the body harnesses.

17 Claims, 10 Drawing Sheets

(51) Int. Cl.
*A61F 5/37* (2006.01)
*A61H 1/02* (2006.01)
*A61H 3/00* (2006.01)
*B25J 9/00* (2006.01)

(52) U.S. Cl.
CPC ......... *A61H 1/0237* (2013.01); *A61H 1/0262* (2013.01); *A61H 1/0274* (2013.01); *B25J 9/0006* (2013.01); *A61H 2003/007* (2013.01); *A61H 2201/1645* (2013.01); *A61H 2201/1652* (2013.01)

(58) Field of Classification Search
CPC ........ A61F 5/30; A61F 5/0102; A61F 5/0106; A61F 5/0109; A61F 5/0112; A61F 5/0118; A61H 2201/1652; A61H 3/008; A61H 2201/1645; A61H 2003/07; A61H 1/00; A61H 3/00; B25J 9/0006
See application file for complete search history.

(56) References Cited

U.S. PATENT DOCUMENTS

| | | | |
|---|---|---|---|
| 6,099,446 | A | 8/2000 | Johnson et al. |
| 6,428,495 | B1 | 8/2002 | Lynott |
| 8,784,285 | B1 | 7/2014 | Lopez et al. |
| 2014/0005798 | A1* | 1/2014 | Bache ................. A61F 2/80 623/33 |
| 2014/0336020 | A1 | 11/2014 | Von Hoffmann et al. |
| 2019/0380856 | A1* | 12/2019 | Hammerslag .......... A43C 11/14 |

FOREIGN PATENT DOCUMENTS

| | | |
|---|---|---|
| JP | 2004-277967 A | 10/2004 |
| JP | 2011-000277 A | 1/2011 |
| JP | 2011-518593 A | 6/2011 |
| WO | 01/28636 A1 | 4/2001 |
| WO | 2009/130511 A1 | 10/2009 |
| WO | 2012/101602 A1 | 8/2012 |
| WO | 2014/109799 A1 | 7/2014 |
| WO | 2014/151065 A2 | 9/2014 |
| WO | 2015/088863 A2 | 6/2015 |

OTHER PUBLICATIONS

Written Opinion of the International Searching Authority for PCT/US2016/019565 dated Jul. 4, 2016, pp. 1-7.
European Search Report, European Patent Application No. 16756358.4, dated Oct. 26, 2018, 9 pages.

* cited by examiner

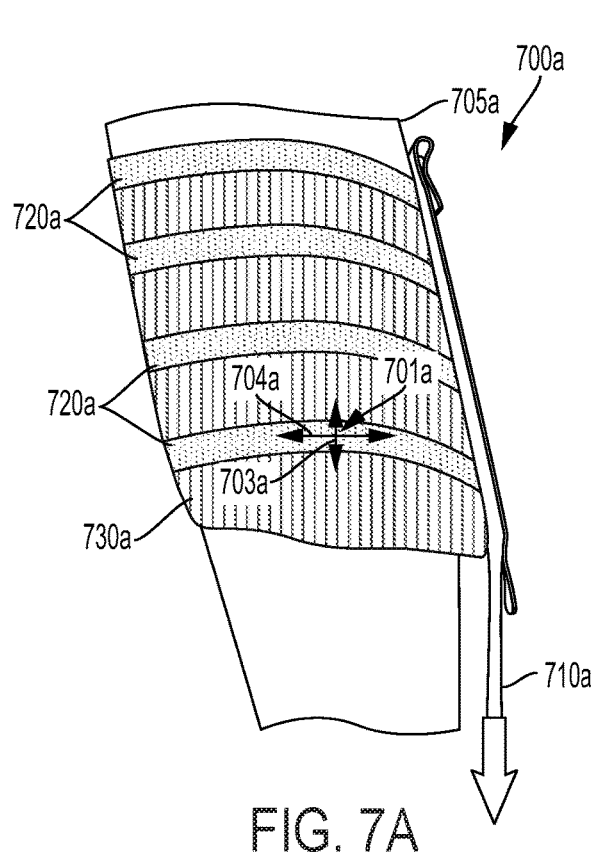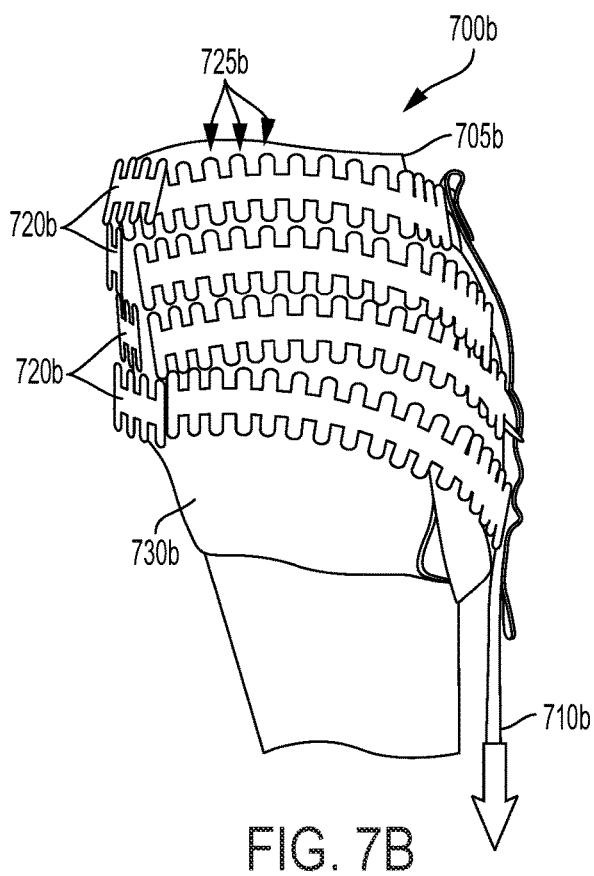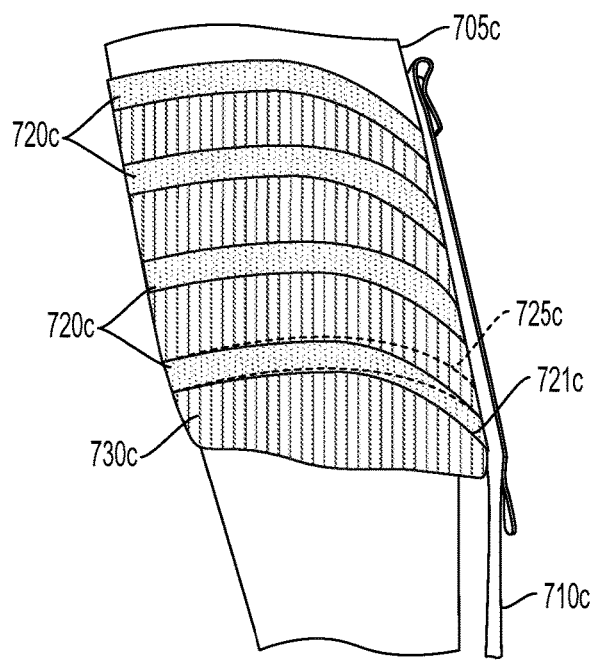

FLEXGRIP

CROSS-REFERENCE TO RELATED APPLICATION

This application is a U.S. national phase of International Application No. PCT/US2016/019565, filed on Feb. 25, 2016, which claims priority to U.S. Provisional Application No. 62/120,794, filed Feb. 25, 2015, both of which are incorporated by reference herein in their entirety.

GOVERNMENT ACKNOWLEDGEMENT

This invention was made in part with Government support under contract P22139 number W911QX-12-C-0049 awarded by the U.S. Army. The Government has certain rights in this invention.

BACKGROUND

Unless otherwise indicated herein, the materials described in this section are not prior art to the claims in this application and are not admitted to be prior art by inclusion in this section.

In many physical activities, a participant in the activity performs to the limit of his or her physical ability, testing the participant's endurance, strength, coordination, shock tolerance, or other physical variables. Warfighters can be expected to carry heavy loads across long distances, taxing their endurance and risking injury due to falls, unstable terrain, or other unanticipated physical shocks. The elderly or the physically disabled can experience difficulty in performing activities of daily living, due to reduced endurance, strength, injury-resistance, balance, or other issues. Movers or other persons engaged in physical labor can be at increased risk of injury due to repeatedly lifting heavy loads over long durations and difficulty coordinating physical efforts (e.g., lifting a large object) between multiple people. Athletes can be exposed to joint, tendon, or other forces sufficient to cause significant temporary or permanent injury. Individuals recovering from surgery or a disabling injury may be unable to perform the minimum tasks necessary to begin rehabilitation, and thus may be barred from recovery. Other examples exist of populations and activities that respectively may require more physical ability than is available to members of the population or to participants in the activities.

Assistive devices may be able to alleviate some of these issues. A variety of assistive devices, including various exoskeleton-based devices, have been developed to increase a user's strength, fatigue resistance, coordination, or other factors. These exoskeletons or other devices can be powered or unpowered, and may be controlled by feedback from the user's movements, be operated in a feed-forward manner, or be completely passive (e.g., hernia belts, lifting harnesses). Assistive devices can include electrical or mechanical actuators, sensors, and controllers. Various assistive devices have been applied to some of the above populations and activities with varying degrees of success.

SUMMARY

Some embodiments of the present disclosure provide a flexible body harness that is mountable to a segment of a body such that the flexible body harness at least partially encloses the segment of the body. The flexible body harness includes: (i) a flexible underlayer; (ii) a tether; and (iii) first and second straps. The first and second straps are coupled to the tether and to the flexible underlayer such that, when the flexible body harness is mounted to the segment of the body such that the flexible body harness at least partially encloses the segment of the body, the first and second straps are disposed along respective first and second trajectories at least partially around the segment of the body. The first and second trajectories around the segment of the body are on respective sides of the flexible body harness relative to the tether. Further, respective angles of the first trajectory and second trajectory relative to the tether increase with distance along the first strap and second strap, respectively, from the tether across at least a respective portion of each of the first strap and the second strap such that, when a force is applied to the flexible body harness via the tether, a shear is applied to skin of the segment of the body, via the first and second straps and the underlayer, that is substantially even across the respective portions of each of the first and second straps.

Some embodiments of the present disclosure provide a flexible body harness that is mountable to a segment of a body such that the flexible body harness at least partially encloses the segment of the body. The flexible body harness includes: (i) a tether; and (ii) first and second straps. The first and second straps are coupled to the tether such that, when the flexible body harness is mounted to the segment of the body such that the flexible body harness at least partially encloses the segment of the body, the first and second straps are disposed along respective first and second trajectories at least partially around the segment of the body. The first and second trajectories around the segment of the body are on respective sides of the flexible body harness relative to the tether. Further, respective angles of the first trajectory and second trajectory relative to the tether increase with distance along the first strap and second strap, respectively, from the tether across at least a respective portion of each of the first strap and the second strap such that, when a force is applied to the flexible body harness via the tether, a shear is applied to skin of the segment of the body, via the first and second straps, that is substantially even across the respective portions of each of the first and second straps. The flexible body harness further includes (iv) a plurality of alignment straps that are woven together with the first and second straps to maintain the first and second straps along the first and second trajectories, respectively, when a force is applied to the flexible body harness via the tether.

Some embodiments of the present disclosure provide a method that includes: (i) mounting a flexible body harness to a segment of a body such that the flexible body harness at least partially encloses the segment of the body. The flexible body harness includes: (a) a flexible underlayer; (b) a tether; and (c) first and second straps. The first and second straps are disposed on the flexible underlayer and are coupled to the tether and to the flexible underlayer such that the first and second straps are disposed along respective first and second trajectories at least partially around the segment of the body. The first and second trajectories around the segment of the body are on respective sides of the flexible body harness relative to the tether. Further, a coupling location between the flexible underlayer and the first strap is adjustable such that the first trajectory can be adjusted. Respective angles of the first trajectory and second trajectory relative to the tether increase with distance along the first strap and second strap, respectively, from the tether across at least a respective portion of each of the first strap and the second strap such that, when a force is applied to the flexible body harness via the tether, a shear is applied to skin of the segment of the body, via the first and second straps and the underlayer. The method further includes: (ii) applying a force to the flexible body harness via the tether; (iii) determining a relative amount of shear applied to skin of the segment of the body, via the first strap and the underlayer, at two or more locations along the first strap; (iv) determining at which of the two or more locations the applied shear is the greatest; and (v) adjusting the strap at the one of the two or more locations at which the applied shear is the greatest such that the shear applied to skin of the segment of the body, via the first strap and the underlayer, at the determined one of the two or more locations is reduced.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7A is a side view of a body harness that is mounted around a calf of a body.

FIG. 7B is a side view of a body harness that is mounted around a calf of a body.

FIG. 7C is a side view of a body harness that is mounted around a calf of a body.

DETAILED DESCRIPTION

Figure 1:
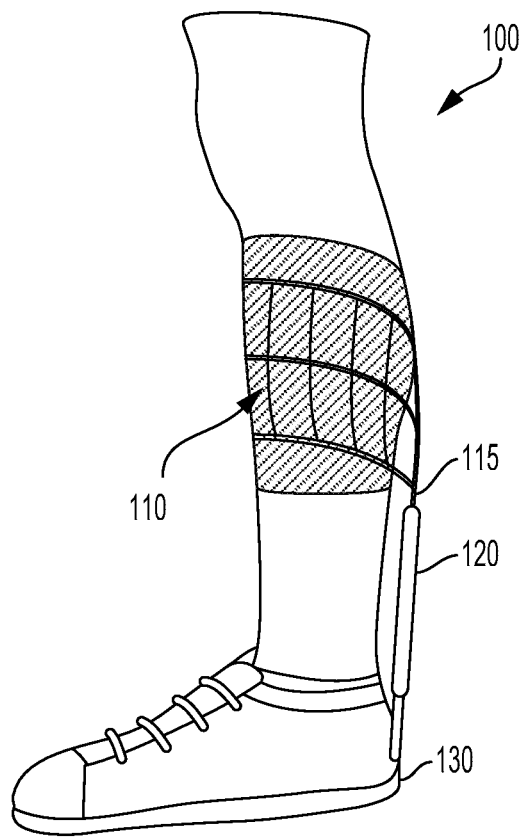
FIG. 1 illustrates a flexible body harness.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Some embodiments of the present disclosure provide a flexible body harness configured to be mounted to the body of a wearer and to apply forces to the body of the wearer, for example, in connection with various physical activities of the wearer. In some examples, the flexible body harness could transmit forces between segments of the body of the wearer to augment forces applied by the musculature of the wearer's body, transmit forces from the wearer's body to a prosthetic device (e.g., an artificial leg, and artificial arm), transmit forces to a load (e.g., a backpack, a heavy tool), transmit forces from a part of a vehicle (e.g., forces exerted from a frame of a hang-glider), transmit forces as part of a surgical or rehabilitative apparatus, or transmit forces to or from one or more segments of a wearer's body according to some other application Such a body harness can be configured to transmit such forces into a body segment of a wearer via skin of the body segment. Such forces can include normal forces (i.e., forces into the surface of the skin) and/or shear forces (i.e., forces parallel to the surface of the skin). However, transmitting too great a normal and/or shear force into any particular area of skin (that is, providing too great a normal and/or shear pressure to the skin at any one location) can cause discomfort and/or injury. Thus, the flexible body harnesses described herein are configured to distribute such forces evenly over areas of skin of body segments to which the flexible body harnesses are mounted, e.g., to provide an increased amount of total force transmitted into the body segment, via the flexible body harness, while maintaining a maximum normal and/or shear pressure applied across any particular area of the skin of the body segment below some maximum value.

In particular, the flexible body harnesses described herein are configured to evenly distribute shear forces and/or pressures applied to skin of such body segments. It is often beneficial to apply forces to a body segment in the direction of the long axis of the body segments such that a substantial portion of the applied force is parallel to the surface of the skin on the body segment. For example, it may be beneficial to transmit forces from the calf of a body, along the long axis of the calf behind the ankle, to facilitate providing forces between the calf and the foot to assist with extension of the ankle and/or to recover energy from the flexion under load of the ankle during locomotion. In another example, it may be beneficial to transmit forces from the calf and the thigh of a body, along the long axes of the calf and the thigh in front of the knee, to facilitate providing forces between the calf and the thigh to assist with extension of the knee and/or to recover energy from the flexion under load of the knee during locomotion. Such forces may be transmitted into skin of a body segment, by a flexible body harness as described herein, as shear forces and/or pressures that are parallel to the direction of the applied force and that are evenly distributed across the skin of the body segment.

This is illustrated by way of example in FIG. 1. FIG. 1 illustrates elements of an assistive system 100 that includes a number of elements configured to provide forces across the ankle of a wearer. The system 100 includes a flexible body harness 110 mounted to the calf segment of the body of the wearer. The flexible body harness 110 is coupled, via a tether 115 or other force-coupling means of the flexible body harness 110, to a transmission element 120 that is, in turn, coupled to a boot 130 mounted to the foot segment of the body of the wearer. The transmission element 120 could include active elements (e.g., a hydraulic cylinder, a linear electric actuator, a twisted string actuator, an electromechanical, electrostatic, hydraulic, or otherwise configured clutch) and/or passive elements (e.g., springs, shock absorbers, elastic cords, pulleys) configured to provide a force between the calf and the foot of the body of the wearer via the flexible body harness 110 and the boot 130, respectively. Such a force, being transmitted between the calf and the foot behind the ankle, could act to provide an extension or plantarflexion torque at the ankle and/or to provide a compressive force at the ankle.

The system 100 illustrated in FIG. 1, includes a transmission element 120 that is attached to a first body harness element that is flexible (i.e., flexible body harness 110) and to a second body harness element that is rigid (i.e., boot 130) and configured to apply forces and/or torques across the ankle of a wearer. However, flexible body harnesses as described herein could be mounted to a variety of different body segments (e.g., a thigh, a foot, an upper arm, a lower arm, a hand, a segment of a finger, a head, a torso, a pelvis) and/or portions of body segments (e.g., an upper torso, a lower torso) and coupled, via actuators, springs, shock absorbers, clutches, or other force-transmitting elements to one or more other body segments, to another portion of a body segment to which the flexible harness is mounted (e.g., from a harness on an upper torso to a harness on a lower torso), to a load or other device (e.g., to a backpack, to a prosthetic, to a tool, to a vehicle), or coupled to some other object(s) or body part(s).

As shown in FIG. 1, forces applied to the calf body segment, via the flexible body harness 110, are in the direction of the long axis of the calf body segment. In such an example, much of the force applied to the calf body segment, via skin of the calf body segment, may be applied to the skin by the flexible body harness 110 as a shear force and/or pressure. The flexible body harness 110 may be configured to apply this shear evenly across an area of the skin, so as to reduce a maximum shear force applied to any one area of the skin due to loading of the flexible body harness 110 by a force of a given magnitude.

In order to distribute such applied forces evenly, such a flexible body harness could include one or more pairs of straps coupled to a tether or other force-transmitting means of the flexible body harness. Each strap is substantially inextensible along its length while being flexible in other directions. Thus, each strap can transmit forces along its length while being able to curve and/or flex, e.g., with changes in the geometry of a body segment to which a flexible body harness including the strap is mounted. The straps could be disposed along respective trajectories at least partway around a body segment, such that when a force is applied, via the tether or other force-transmitting means, to the flexible body harness, a shear is applied substantially evenly to skin of the body across portions of each of the straps. Such portions could include the entirety of one or more of the straps, a portion of one or more of the straps that is proximate to the attachment of the strap(s) to the tether, and/or a portion of one or more of the straps that is distal from the attachment of the strap(s) to the tether. The trajectories of each strap of a pair of straps of such a flexible body harness could travel around the body segment on opposite sides of the flexible body harness relative to the tether, e.g., to balance forces applied to the tether that may displace the location of the tether around the body segment. The evenly applied shear force and/or pressure could be primarily applied in a direction parallel to the force applied to the tether or other force-transmitting means of the flexible body harness.

The trajectories of such straps could be specified according to additional considerations. For example, the trajectory of a strap of a flexible body harness as described herein could be specified such that the strap does not slip on a body segment to which the harness is mounted. That is, the trajectory of the strap could be specified such that the normal force and/or pressure exerted at each location along the strap is sufficiently large, relative to the shear force and/or pressure exerted at each location along the strap, that the flexible body harness does not slip relative to the skin.

Applying a shear substantially evenly across a portion of a strap of a flexible body harness as described herein could include applying a range of shear forces and/or shear pressures to respective locations along the portion of the strap that vary, with respect to some measurement of variation of the shear across the portion of the strap, by less than some specified amount. For example, a difference between a maximum shear force and/or shear pressure applied to the skin along the portion of the strap and a minimum shear force and/or shear pressure applied to the skin along the portion of the strap could be less than a specified amount, e.g., less than 10%. Such a pattern of shear applied to skin of a segment of a body, across a portion of a strap of a flexible body harness, could be said to vary by less than 10%. In another example, a rate of change of the applied shear force with change in location along the strap could be, at no location across the portion of the strap, greater than some specified maximum.

Trajectories of straps of such a flexible body harness around a body segment could correspond to a variety of shapes, determined and/or set according to a variety of methods, such that, when the flexible body harness is mounted to a body segment to at least partially enclose the body segment and force is being applied via a tether of the flexible body harness, shear (e.g., shear pressure) is applied to skin of the segment of the body, via the straps, that is substantially even across portions of each strap. In some examples, the portion across which the shear is evenly applied could include substantially all of a strap (e.g., all of the strap that is in contact with and/or proximate to skin of the body segment). In order to apply shear pressure evenly, the angle of such a strap, relative to the tether through which force is applied (and thus relative to the direction of the applied force), could increase with distance from the tether across such a portion of the strap. In such a configuration, the shear pressure applied from the strap to the skin (e.g., directly, or through an underlayer or other element(s) of the flexible body harness) could have substantially the same magnitude at each location across the portion of the strap. That is, the shear could be applied evenly across the portion of the strap.

Figure 2:
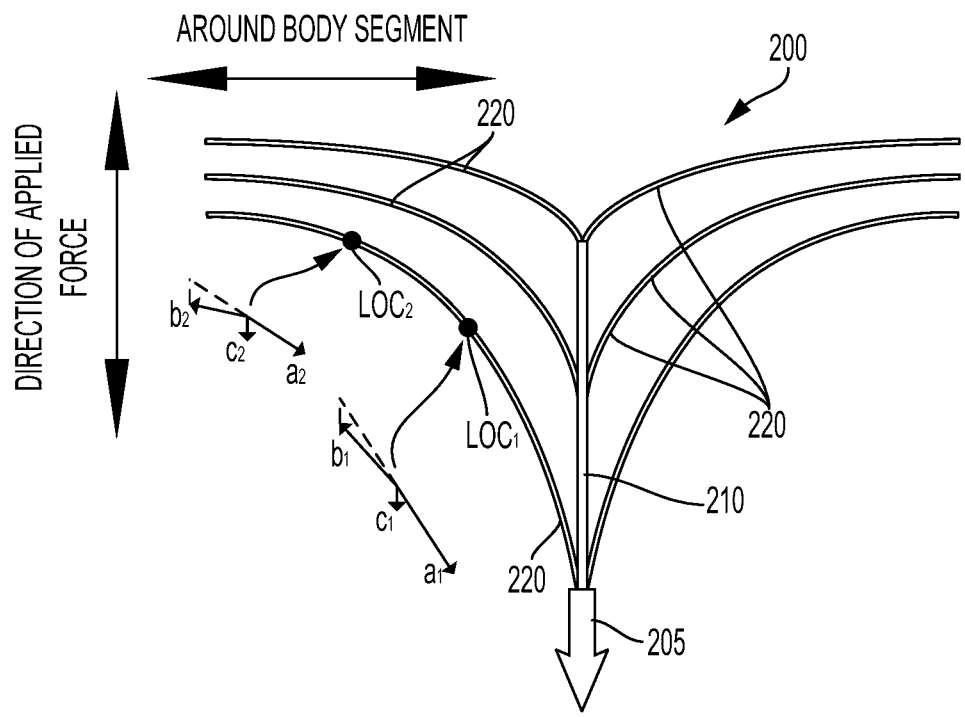
FIG. 2 illustrates the trajectories of straps of a flexible body harness around a body segment.

Examples of such trajectories are illustrated by way of example in FIG. 2. FIG. 2 shows a schematic of a flexible body harness 200 configured in such a manner. The harness 200 includes a number of straps 220 coupled to a tether 210. As shown in FIG. 2, the trajectories of the straps 220 are unwrapped from a body segment to which the harness 200 may be mounted. The direction of a force 205 that may be applied to the harness 200, via the tether 210, that may in turn be evenly applied to skin of a body segment across portions of the straps 220, is indicated by the vertical arrow ("DIRECTION OF APPLIED FORCE"). The horizontal arrow ("AROUND BODY SEGMENT") indicates the direction of displacement around the body segment, when the harness 200 is mounted to such a body segment.

The illustrated trajectories of the straps 220 in FIG. 2 may be trajectories that completely enclose a body segment (e.g., the ends of the illustrated straps could be coupled together on a side of the body segment opposite the tether 210 by snaps, ties, a knot, an adhesive, or some other means for coupling the ends of a pair of straps and/or opposing straps could comprise a single continuous strap that encloses the body part and that is coupled, at its ends, to the tether 210). Alternatively, the illustrated trajectories could partially enclose a body segment (e.g., the ends of the straps 220 could be tethered to an underlayer and/or the straps could continue around the body segment, to meet with the end of corresponding straps, to couple to a clasp or other means for mounting and unmounting the harness 200 to the body segment) or could encircle the body segment repeatedly (e.g., a particular strap could, following an illustrated trajectory, wrap around the body segment fully one or more times before meeting with the end of an opposite strap, coupling with a clasp, coupling to an underlayer, or otherwise terminating).

The trajectory of a particular strap may be specified such that, at multiple different locations on the particular strap, the shear applied directly or indirectly to the skin by the strap at the multiple different locations (e.g., the shear force and/or shear pressure applied at the multiple different locations) is substantially the same. This is illustrated by the example locations "$LOC_1$" and "$LOC_2$" on the same strap 220 of the harness 200 in FIG. 2. The tension along the strap in both directions ($a_1$ and $a_2$ in the direction toward the strap, $b_1$ and $b_2$ in the direction away from the strap), as well as the shear force exerted by the strap directly or indirectly into skin of the body segment ($c_1$ and $c_2$) are illustrated, for each of the locations, by respective force diagrams. As the strap 220 is capable of transmitting forces along its length, but is flexible in perpendicular directions, the forces transmitted along the strap (e.g., as tensions $a_1$, $a_2$, $b_1$, $b_2$ in the strap along the length of the strap) are oriented in the directions of the strap as it moves away from each location. As the trajectory of the strap 220 is such that the angle of the strap, relative to the tether 210, increases with distance from the tether 210, the angles of these forces transmitted along the strap are not the same, and thus a residual force ($c_1$, $c_2$) may be exerted, from the strap at each location, into the skin directly or indirectly (e.g., as a shear force or pressure). As shown in FIG. 2, the trajectory of a strap 220 may be specified such that these residual forces are substantially the same across a portion of the strap (illustrated in FIG. 2 by the equal magnitudes of $c_1$ and $c_2$) such that shear may be exerted evenly across the portion of the strap (e.g., across all of the strap, across a portion of the strap proximal to the tether 210).

Note that the illustrated trajectories and forces represent locations in three-dimensional space along the external surface of a body segment (e.g., locations on the skin of a body segment) projected onto the two-dimensional plane of the Figure. In practice, trajectories of straps of a flexible body harness as described herein will, when the harness is mounted at least partially around a body segment of a wearer, have a three-dimensional shape. Further, the forces exerted by such straps into the skin may include both forces parallel to the surface of the skin (i.e., shear forces and/or pressures) and normal to the surface of the skin (i.e., compressive forces and/or pressures into the skin).

The trajectories of straps of a flexible body harness as described herein (e.g., straps 220) could assume and/or include a variety of shapes such that, when the harness is mounted to a body segment and force is applied, via a tether or other loading means, shear is applied evenly to skin of the body segment across portions of the straps. In some examples, portions of the trajectories could correspond to sections of catenary curves. For example, if the geometry of the surface of a body segment approximates a cylinder, a strap following a trajectory along the outside of the body segment that corresponds to half of a catenary curve could, when loaded via a tether, evenly apply shear to skin of the body segment across the portion of the strap whose trajectory corresponds to the half of the catenary curve. Other trajectories of a strap, incorporating other shapes, could be used to evenly distribute forces exerted by the strap across some or all of the length of the strap. Such trajectories could be determined based on a model of a corresponding body segment (e.g., based on a cylindrical geometry, based on a measured geometry of a body segment of a particular wearer, based on a calculated average geometry of a body segment of a population of individuals). Additionally or alternatively, the flexible body harness could be adjustable such that the trajectory of one or more straps of the harness can be adjusted, e.g., to increase a degree to which forces exerted by the strap into skin are evenly distributed across one or more portions of the strap.

As noted above a pair of straps of a flexible body harness could form a single continuous strap that fully encloses a body segment of a wearer. The straps could follow respective trajectories, based on the geometry or other properties of the body segment, such that one or more portions of each of the straps evenly exert a shear onto skin of the body segment along the respective portions of each of the straps. As described above, such trajectories could include segments wherein the angle of the strap, relative to the tether of the harness to which the straps are coupled, increases with distance along the strap from the tether. Such trajectories could correspond to a segment of a catenary curve, e.g., if the surface of the body segment is approximately cylindrical.

Figure 3A:
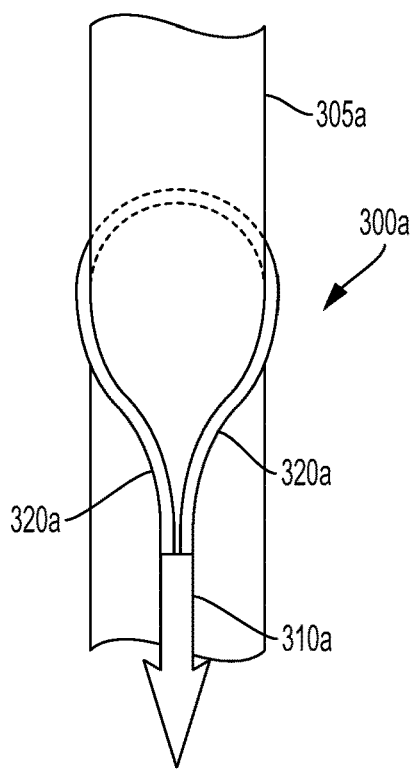
FIG. 3A is a back view of an example body harness that is mounted around a cylindrical body segment.
Figure 3B:
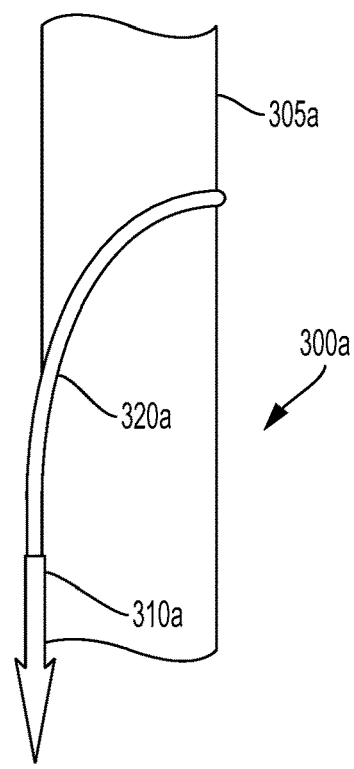
FIG. 3B is a side view of the example body harness shown in FIG. 3A

This is illustrated by way of example in FIGS. 3A and 3B. FIG. 3A shows a front view of a flexible body harness 300a that is mounted to fully enclose an approximately cylindrical body segment 305a. FIG. 3B shows a side view of the flexible body harness 300a and the body segment 305a. The flexible body harness 300a includes a tether 310a via which forces may be applied to the flexible body harness 300a. The flexible body harness 300a also includes a continuous strap 320a that is coupled at both ends to the tether 310a and that follows a trajectory around the body segment 305a such that, when a force is applied to the harness 300a via the tether 310a, a shear is evenly applied to skin of the body segment 305a via the strap(s) 320a. As shown in FIGS. 3A and 3B, the angle of the strap 320a, relative to the tether 310a, increases with distance along the strap 320a from the tether 310a until the angle of the strap 320a is orthogonal to the tether 310a (e.g., on the opposite side of the body segment 305a from the tether 310a). The shape of the trajectory of the strap 320a could correspond to a section of a catenary curve that has been wrapped around the body segment 305a.

Figure 3C:
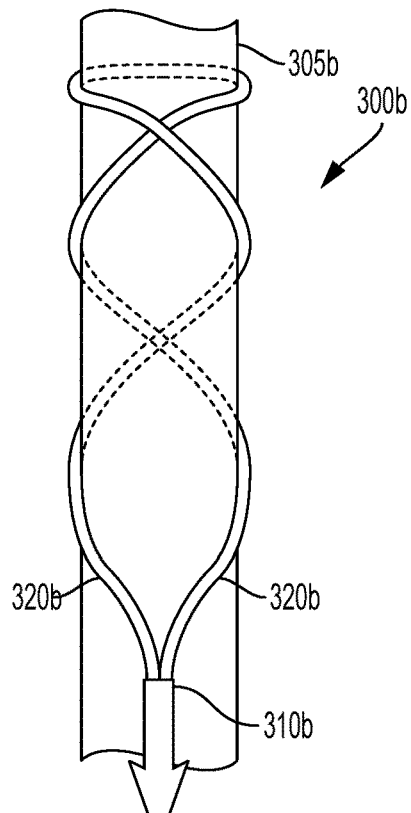
FIG. 3C is a back view of an example body harness that is mounted around a cylindrical body segment.
Figure 3D:
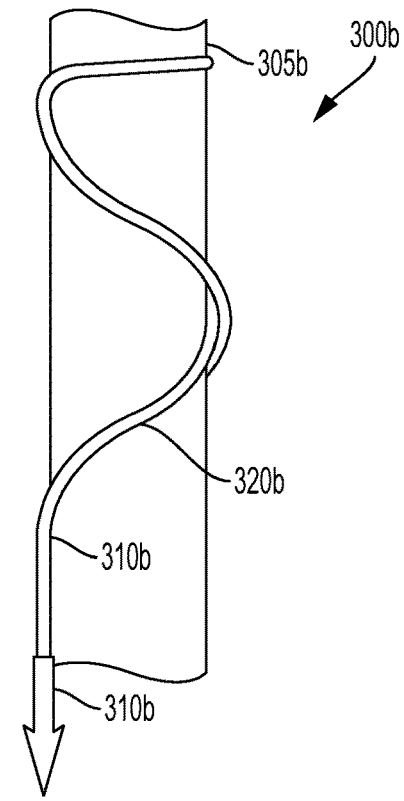
FIG. 3D is a side view of the example body harness shown in FIG. 3C

A strap of such a flexible body harness could wrap around a body segment multiple times. A flexible body harness could be configured in this way to increase an area and/or length of such a strap over which a force applied to the harness may be distributed, as a shear and/or normal force, into skin of the body segment. This is illustrated by way of example in FIGS. 3C and 3D. FIG. 3C shows a front view of a flexible body harness 300b that is mounted to fully enclose an approximately cylindrical body segment 305b. FIG. 3D shows a side view of the flexible body harness 300b and the body segment 305b. The flexible body harness 300b includes a tether 310b via which forces may be applied to the flexible body harness 300b. The flexible body harness 300b also includes a continuous strap 320b that is coupled at both ends to the tether 310b and that follows a trajectory that wraps around the body segment 305b multiple times such that, when a force is applied to the harness 300b via the tether 310b, a shear is evenly applied to skin of the body segment 305b via the strap(s) 320b. As shown in FIGS. 3C and 3D, the angle of the strap 320b, relative to the tether 310b, increases with distance along the strap 320b from the tether 310b until the angle of the strap 320b is orthogonal to the tether 310b (e.g., on the opposite side of the body segment 305b from the tether 310b). The shape of the trajectory of the strap 320b could correspond to a section of a catenary curve that has been wrapped around the body segment 305b multiple times.

Note that a flexible body harness as described herein could include multiple pairs of straps coupled to a tether (and/or multiple continuous straps that enclose a body segment and that are coupled at both ends to such a tether) and disposed at least partially around a body segment to which the harness is mounted along respective trajectories such that, when a force is applied to the tether, the straps apply substantially evenly distributed shears across respective portions of each of the straps (e.g., as illustrated in FIG. 2). Further, a flexible body harness configured to mount to a particular body segment could include multiple tethers, with corresponding sets of straps, configured to allow force to be applied to each of the multiple tethers and to distribute such applied force evenly across portions of straps of the harness. Yet further, such flexible body harnesses could be configured in a variety of ways to maintain the trajectories of the straps such that forces are applied evenly across portions of the straps (e.g., by weaving the straps with each other and/or with a set of alignment straps, by coupling the straps to a flexible underlayer or other garment or material, by forming the straps on or within a flexible underlayer or other garment or material) when a force is applied to a tether of the harness.

Multiple harnesses, configured to mount at least partially around multiple respective body segments, could be incorporated into a single flexible system, e.g., a flexible garment, to facilitate mounting and dismounting the harnesses to the respective body segments. Such a system could include one or more hydraulic cylinders, linear electric actuators, twisted string actuators, electromechanical, electrostatic, hydraulic, otherwise configured clutches, springs, shock absorbers, elastic cords, pulleys, or other active and/or passive force-transmitting elements coupled between tethers of respective different flexible body harnesses of the system, e.g., to transmit forces, via the different harnesses, between respective different body segments of a wearer when the system is mounted to (e.g., being worn by) such a wearer. Such a system could further include motor drivers, hydraulic pumps, electrostatic generators, sensors, batteries, control interfaces, controllers, or other elements configures to provide some functionality of the system (e.g., to provide assistive forces to the body of the wearer via the flexible body harnesses of the system)

II. Example Flexible Body Harnesses

A flexible body harness as described herein could be configured in a variety of ways such that, when the flexible body harness is mounted at least partially around a body segment, a force applied to a tether or other load-transmitting means of the harness can be evenly applied to skin of the body segment across one or more portions and/or substantially all of one or more straps of the flexible body harness. Further, such a flexible body harness could include additional elements and/or could be configured to provide further functionality, e.g., to facilitate donning and doffing of the harness, to maintain the straps of the harness along respective trajectories such that the straps can evenly apply shear forces and/or pressures or other forces to skin of the body segment, to distribute such applied forces over larger areas further from the straps, to facilitate adjustment of the trajectories of the straps, to wick moisture away from the skin and/or to provide insulation, protection from blades or projectiles, to inhibit bacteria and/or fungus, or to provide some other functionality.

In some examples, a flexible body harness could include a flexible underlayer. Straps of the flexible body harness could be coupled to the flexible underlayer to facilitate transmission of shears or other forces from the straps, via the flexible underlayer, to skin of a body segment, to maintain the trajectories of the straps relative to such a body segment, or to provide some other functionality. Such a flexible underlayer could have a flexibility and/or compliance that differs from that of the straps (e.g., that is less than that of the straps, at least in a direction along the straps), such that the straps can transmit forces along their length and evenly distribute shear forces and/or pressures, via the flexible underlayer, to skin of a body segment to which a flexible body harness is mounted.

Further, such a flexible underlayer could be configured to provide additional functionality. The material of the flexible underlayer could include anti-bacterial, anti-fungal, or other agents (e.g., silver nanoparticles) to prevent the growth of microorganisms. The flexible underlayer could be configured to manage the transport of heat and/or moisture (e.g., sweat) from a wearer to improve the comfort and efficiency of activity of the wearer. The flexible underlayer could include straps, seams, hook-and-loop fasteners, clasps, zippers, or other elements configured to maintain a specified relationship between elements of the flexible body harness (e.g., straps, tethers, the flexible underlayer itself) and aspects of a wearer's anatomy. This could additionally increase the ease with which a wearer could don and/or doff the flexible body harness and/or a system (e.g., a flexible exosuit system) or garment that includes the flexible body harness. The flexible underlayer could additionally be configured to protect the wearer from ballistic weapons, sharp edges, shrapnel, or other environmental hazards (by including, e.g., panels or flexible elements of para-aramid or other high-strength materials).

Figure 4B:
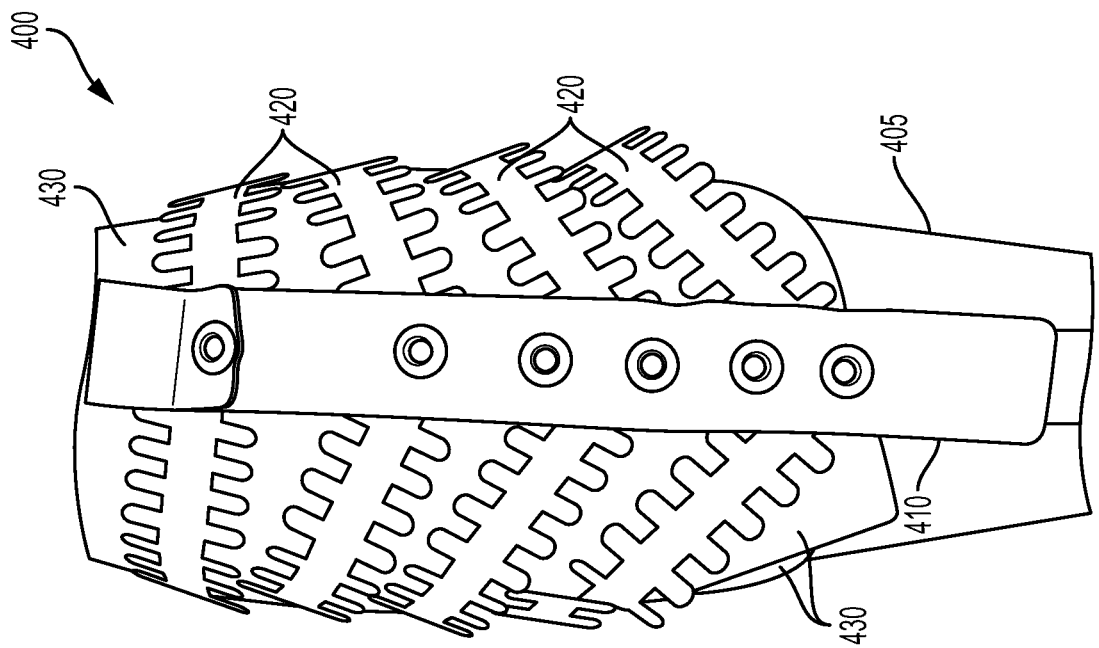
FIG. 4B is a back view of the body harness shown in FIG. 4A
Figure 4A:
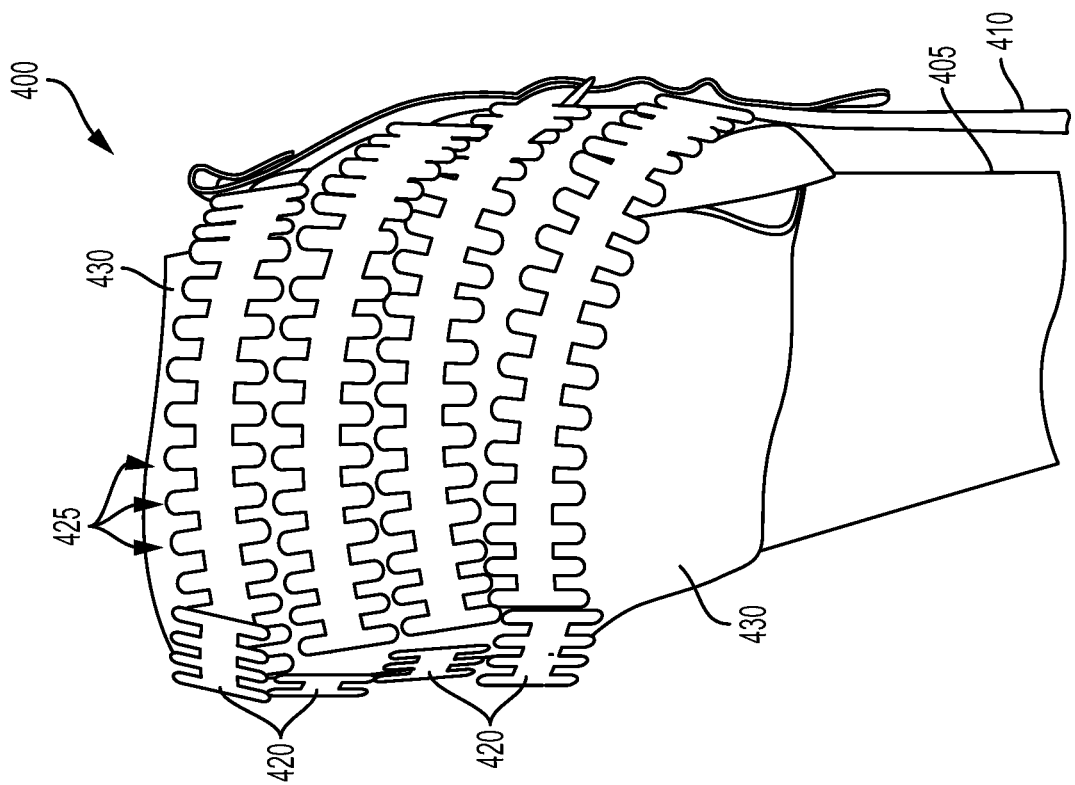
FIG. 4A is a side view of a body harness that is mounted around a calf of a body.

In some examples, the straps (and/or tether) of a flexible body harness could be disposed on the flexible underlayer of the flexible body harness. As noted above, the flexibility of such a flexible underlayer, at least in a direction along the straps, could be less than the flexibility of the straps along the length of the straps, e.g., to facilitate the straps transmitting tensions along their lengths and/or the straps evenly distributing shear forces and/or pressures, via the flexible underlayer, into skin of a body segment. The straps of such a flexible body harness could be attached to the flexible underlayer by stitching, adhesive, snaps or buttons, further straps, ties, a layer of hook-and-loop fasteners. A side view and a front view of an example of such a flexible body harness are shown in FIGS. 4A and 4B, respectively. The flexible body harness 400 is mounted to enclose a body segment 405 (e.g., a calf). The flexible body harness 400 includes four pairs of straps 420 that are coupled to a tether 410 and to a flexible underlayer 430. The straps 420 are disposed on the flexible underlayer 430 along respective trajectories as described herein such that, when a force is applied to the flexible body harness 400 via the tether 410, a shear is applied to skin of the body segment 405, via the straps 420 and the underlayer 430, that is substantially even across respective portions of each of the straps 420 (e.g., that is substantially even across all of each of the straps 420).

As shown in FIGS. 4A, and 4B, the straps 420 are coupled to the flexible underlayer 430 by a layer of hook and loop fasteners. In particular, a plurality of hooks are disposed on the underside of the straps 420 such that the hooks can removably couple to the material of the flexible underlayer 430. Thus, a coupling location between the flexible underlayer 430 and each of the straps can be adjusted in order to adjust the trajectories of the straps 420 around the body segment 405. Pairs of the straps 420 may follow overlapping trajectories and such overlapping straps may couple together at the intersection of the overlapping trajectories, e.g., to allow residual tensions at the end of pairs of the straps 420 to be transferred between the straps of each pair such that the ends of the straps 420 remain in place on the flexible underlayer 430 and are not displaced around the body segment 405. The straps 420 each include a plurality of projections 425 configured to distribute forces from the straps 420 into the skin of the body segment 405 via the flexible underlayer 430.

Note that the flexible body harness 400 illustrated in FIGS. 4A and 4B is intended as a non-limiting example of a flexible body harness that includes pairs of straps disposed on a flexible underlayer. For example, straps of such a harness could be coupled to an underlayer by some other means, e.g., snaps, stitching, adhesive, or some other coupling means. Further, the straps of such a harness may lack the illustrated force-distributing projections 425 and/or may include some additional or alternative means for distributing forces from straps of the harness into a flexible underlayer and/or into skin of a body segment. Yet further, such a flexible body harness could include more or fewer pairs of straps coupled to a tether and/or could include further sets of tethers and associated straps, e.g., to provide for coupling of forces in multiple directions and/or from multiple locations of a body segment to which such a flexible body harness is mounted.

In some examples, the straps (and/or tether) of a flexible body harness could be formed within the flexible underlayer of the flexible body harness. The straps of such a flexible body harness could be formed from a material that is disposed on or within the fabric or other material composing the flexible underlayer. For example, the flexible underlayer could include a layer of fabric, and the straps can be formed from a polymer, resin, or other material deposited on or within the weave of the fabric of the underlayer and dried, cured, or otherwise formed into straps that are integrated into the underlayer material. In another example, the straps of a flexible body harness could be woven into fabric or other material of a flexible underlayer. For example, the flexible underlayer could be woven from a first variety of thread, wire, or other material and the straps could be formed from a second variety of thread, wire, or other material woven through the first type of material. Additionally or alternatively, the straps could be formed from regions of a woven underlayer material that has a denser weave, that has a different weave pattern, or that is otherwise modified, relative to other portions of the flexible underlayer, such that the strap portions can transmit forces, along respective trajectories, as described elsewhere herein. Note that the flexibility of portions of such a flexible underlayer that do not comprise the straps of such a flexible body harness, at least in a direction along the straps, could be less than the flexibility of such strap portions along the length of the straps, e.g., to facilitate the strap elements formed in the flexible underlayer transmitting tensions along their lengths and/or such strap elements evenly distributing shear forces and/or pressures into skin of a body segment.

Figure 5:
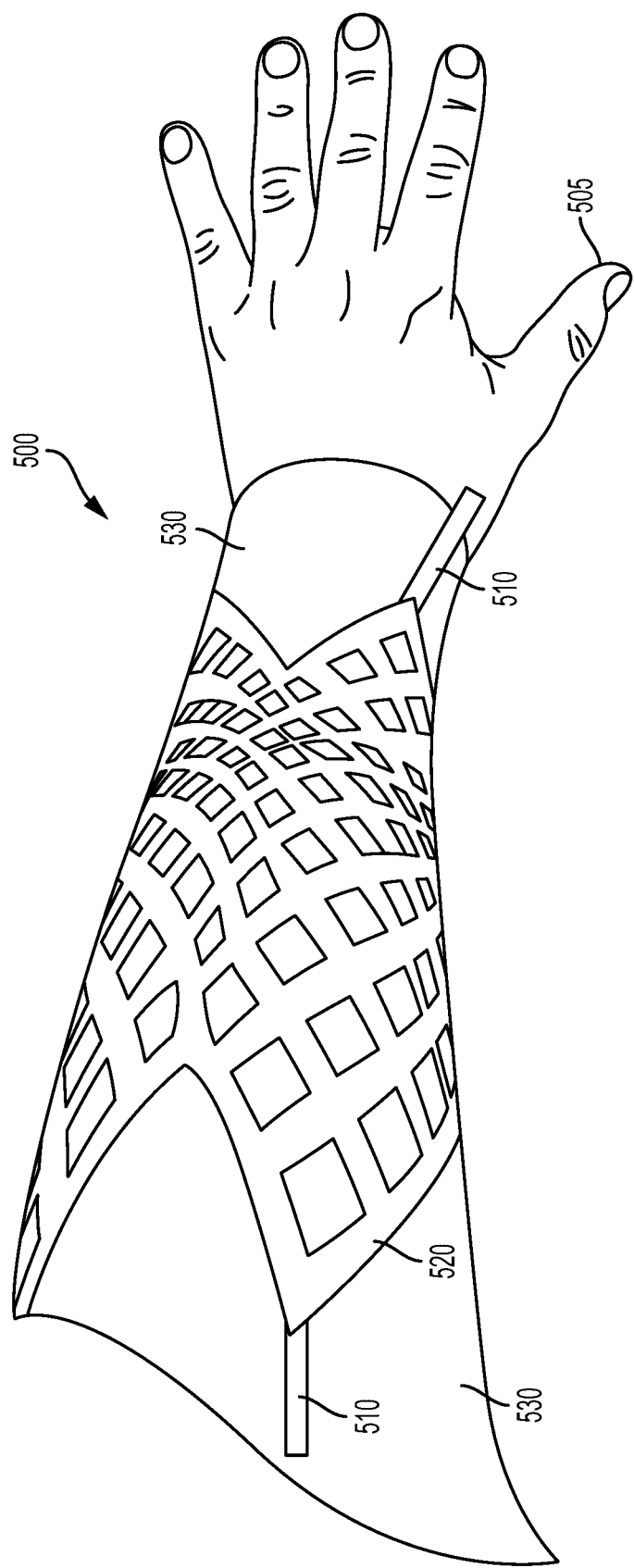
FIG. 5 is a perspective view of a body harness that is mounted around a forearm of a body.

Such a flexible body harness is shown in FIG. 5. The flexible body harness 500 is mounted to enclose a body segment 505 (e.g., a forearm). The flexible body harness 500 includes a pattern of straps 520 formed within the flexible underlayer 530. The pattern of straps 520 could be a polymer material formed within a woven fabric of the flexible underlayer 530. In another example, the pattern of straps 520 could be composed of thread, wire, or other material woven into, within, or through a fabric, rubber, polymer, or other material of the flexible underlayer 530. In yet another example, the pattern of straps 520 could be regions of a fabric of the flexible underlayer 530 wherein the weave of the fabric is denser, wherein the pattern of the weave is different, or wherein some other property of the fabric is different, relative to other regions of the flexible underlayer 530 such that the strap portions can transmit forces, along respective trajectories, as described elsewhere herein. The pattern of straps 520 formed within the flexible underlayer 530 is coupled to tethers 510. The pattern of straps 520 are configured to correspond to trajectories as described herein such that, when a force is applied to the flexible body harness 500 via one or both of the tethers 510, a shear is applied to skin of the body segment 505, via the patterns of straps 520 and the underlayer 530, that is substantially even across respective portions of straps within the pattern of straps 520 (e.g., that is substantially even across all of each of a number of trajectories through the pattern of straps 520).

Note that the flexible body harness 500 illustrated in FIG. 5 is intended as a non-limiting example of a flexible body harness that includes pairs of straps formed within a flexible underlayer. For example, such a flexible body harness could include more or fewer pairs of straps, formed as a different pattern of straps, coupled to a tether and/or could include further sets of tethers and associated straps and/or trajectories through a pattern of straps, e.g., to provide for coupling of forces in multiple directions and/or from multiple locations of a body segment to which such a flexible body harness is mounted.

Figure 6:
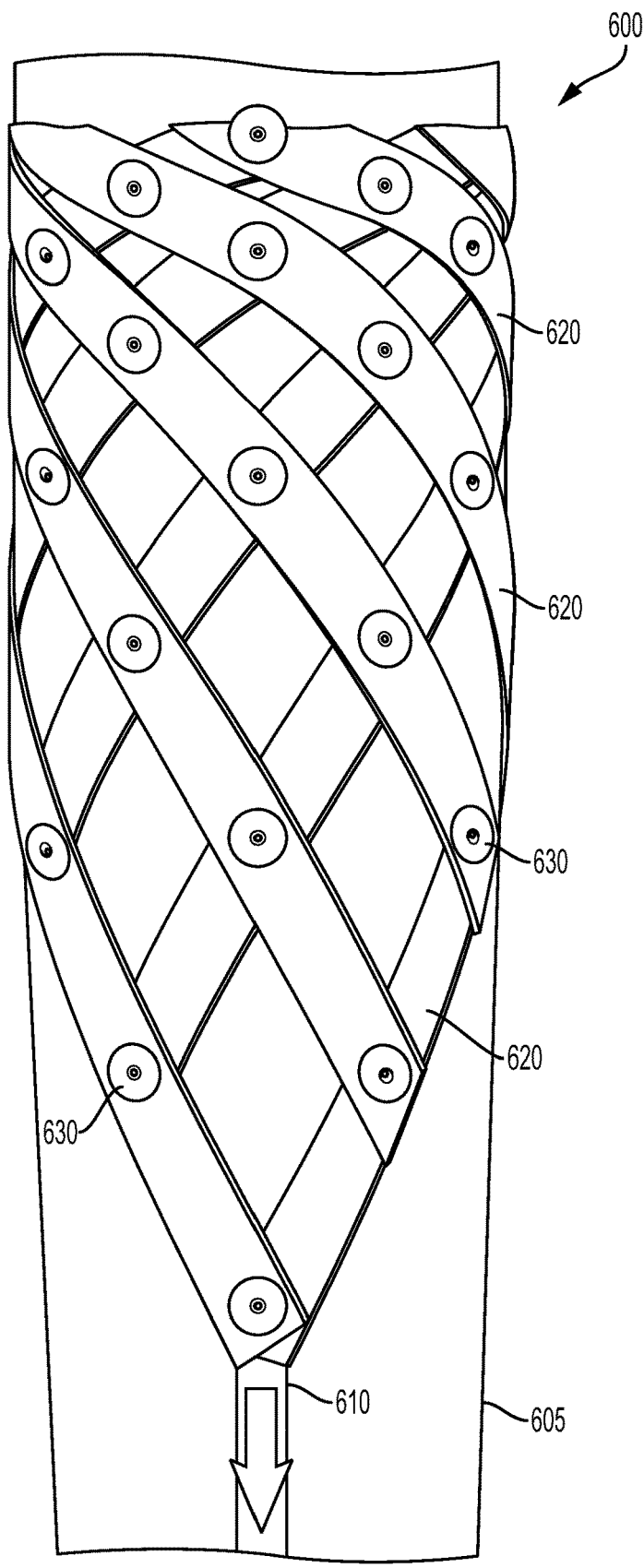
FIG. 6 is a back view of a body harness that is mounted around a calf of a body.

In some examples, the load-bearing straps of a flexible body harness could be woven together and/or woven together with a plurality of further alignment straps such that the load-bearing straps of the flexible body harness are maintained along respective trajectories when the flexible body harness is mounted to a segment of a body. Such a flexible body harness is shown in FIG. 6. The flexible body harness 600 is mounted to enclose a body segment 605 (e.g., a calf). The flexible body harness 600 includes pairs of straps 620 that are coupled to a tether 610 and that are woven together. A subset of the straps 620 are load-bearing straps that are disposed along respective trajectories as described herein such that, when a force is applied to the flexible body harness 600 via the tether 610, a shear is applied to skin of the body segment 605, via the load-bearing straps 620, that is substantially even across respective portions of each of the load-bearing straps 620 (e.g., that is substantially even across all of each of the load-bearing straps 620). Another subset of the straps 620 are alignment straps that are woven together with the load-bearing straps to maintain the load-bearing straps along respective trajectories.

As shown in FIG. 6, the straps 620 are coupled to each other via brads 630. Each brad 630 is configured to maintain the relative location of two or more straps (e.g., between load-bearing straps, between alignment straps, and/or between one or more load-bearing straps and one or more alignment straps). Alternatively, forces could be transmitted between straps and/or the relative location between straps could be maintained by some other coupling means, e.g., stitching, knots, hook and loop fasteners, rubber bands, or adhesives. Further, while a brad is indicated at each crossing of the straps 620 of the example flexible body harness 600, a brad (or other coupling means) could be located at a subset of crossing of straps of a flexible body harness. For example, a brad could be located only at the crossings of load-bearing straps, while alignment straps are maintained relative to each other and/or to load-bearing straps by being looped around each other and/or a load-bearing strap, by being connected to each other and/or to a load-bearing strap by hook and loop fasteners, or by being secured in some other way.

Note that the flexible body harness 600 illustrated in FIG. 6 is intended as a non-limiting example of a flexible body harness that includes pairs of straps maintained along respective trajectories by being woven together with alignment straps. For example, such a harness could include an underlayer on which such straps are disposed (e.g., to which the straps are coupled by snaps, stitching, adhesive, or some other coupling means). The straps of such a flexible body harness could be coupled to such a flexible underlayer to transmit shears or other forces into skin of a body segment, to maintain the trajectories of straps of the harness, to wick moisture away from the skin, to protect the skin, or to provide some other functionality. Yet further, such a flexible body harness could include more or fewer pairs of straps coupled to a tether and/or could include further sets of tethers and associated straps, e.g., to provide for coupling of forces in multiple directions and/or from multiple locations of a body segment to which such a flexible body harness is mounted.

A. Example Means for Distributing Forces from Straps of a Harness into Skin of a Body Segment A flexible body harness as described herein includes two or more straps configured to even apply a shear or other forces into skin of a body segment when a force is applied to a tether or other force-coupling means of the flexible body harness. Such a flexible body harness could include further elements (e.g., battens, force-distributing fabrics) configured to further distribute such transmitted shears or other forces over a wider area of skin of the body segment. Additionally or alternatively, straps of such a flexible body harness could be configured to distribute such transmitted shears or other forces over a wider area of skin of the body segment (e.g., by including protrusions or petals configured to distribute forces applied from the straps while permitting the straps to curve along respective trajectories).

In a first example, the flexible body harness could include a flexible underlayer on which the straps of the body harness are disposed. The material of the flexible underlayer could have a pattern of flexibility such that shears transmitted into the skin, via the flexible underlayer, are distributed across a wider area by the flexible underlayer. In particular, the flexible underlayer could be substantially less flexible, at a particular location along a strap of the body harness, in the direction of a shear transmitted from the strap (e.g., in a direction perpendicular to the direction of the strap at the particular location) than in the direction of the strap at the particular location. This is illustrated in FIG. 7A, which shows a flexible body harness 700a mounted to a segment of a body 705a (e.g., a calf). The flexible body harness 700a includes pairs of straps 720a that follow respective trajectories at least partially around the body segment 705a and that are coupled to a tether 710a and to a flexible underlayer 730a. The flexible underlayer 730a is elastically anisotropic; that is, the material of the flexible underlayer 730a is less flexible in a first direction (indicated by the vertical lines) than in a second direction that is substantially orthogonal to the first direction. As such, forces applied to the flexible underlayer 730a in the first direction may be distributed to skin of the body segment 705a over a wider area (e.g., due to the flexible material being more rigid in the first direction and thus being able to transmit the applied forces over a wider area in the first direction) than forces applied to the flexible underlayer 730a in the second direction (e.g., due to the flexible material being more flexible in the second direction and thus being less able to transmit the applied forces over a wider area in the second direction).

This is illustrated in FIG. 7A at a first location 701a along a strap 720a of the flexible body harness 700a. At the first location 701a, the flexible underlayer is substantially more flexible in the direction of the strap 704a than in a direction perpendicular to the direction of the strap 703a (e.g., has an elasticity that is at least 80% greater in the direction of the strap 704a than in the direction perpendicular to the strap 703a). As shown in FIG. 7A, a flexible underlayer of a flexible body harness could be composed of a piece of material that is anisotropically flexible in the same way, and in the same direction, across the entire material of the flexible underlayer. Alternatively, the weave or other properties of the material of the flexible underlayer could be configured such that the direction and/or magnitude of the anisotropy of the flexibility of the flexible underlayer varies across the flexible underlayer, e.g., such that the flexible underlayer is substantially more flexible in the direction of a strap of the flexible body harness than in a direction perpendicular to the direction of the strap at a variety of locations of the strap, e.g., across substantially all of such a strap.

In another example, the flexible body harness could include elements coupled to the straps of the body harness that are configured to distribute forces from the straps into skin of a body segment and/or into a flexible underlayer or other element(s) of the harness that are configured to transmit forces into skin of the body segment. This could include rigid or semi-rigid battens being coupled to the straps and/or to the flexible underlayer of the flexible body harness to distribute forces from straps of the body harness, via each batten, across a wider area. Additionally or alternatively, the width of the straps could be effectively increased. This could include forming the straps to include a plurality of projections that are configured to distribute a shear applied to skin of the segment of the body from the straps. The presence of such projections can effectively increase the area over which a strap directly or indirectly (e.g., via a flexible underlayer) exerts a shear or other force on skin of a body segment while still allowing the strap to follow a curved trajectory as described herein (e.g., such that the strap applies a shear to skin evenly across a portion of the strap) without resulting in the strap buckling or folding.

This is illustrated in FIG. 7B, which shows a flexible body harness 700b mounted to a segment of a body 705b (e.g., a calf). The flexible body harness 700b includes pairs of straps 720b that follow respective trajectories at least partially around the body segment 705b and that are coupled to a tether 710b and to a flexible underlayer 730b. The straps 720b each include a plurality of projections 725b that are configured to distribute a shear applied to skin of the body segment 705b from the straps 720b via the underlayer 730b when the flexible body harness 700b is mounted to the segment of the body 705b and a force is applied to the flexible body harness 700b via the tether 710b. As such, forces applied to the body segment 705b may be distributed to skin of the body segment 705b over a wider area (e.g., due to the forces being applied over a wider area that includes the area of the projections 725b). The illustrated straps 720b, which include the projections 725b, may retain the ability to curve and follow high-curvature trajectories, similar to a strap having a width equal to the width of the straps 720b without the projections 725b, while distributing load similarly to a solid strap having the same width as the full with of the straps 720b extended by the width of the projections 725b.

Note that the addition of such projections to straps of a flexible body harness wherein such straps are disposed on (or within) a flexible underlayer is intended as a non-limited example. Alternatively, such projections could be formed on straps of a flexible body harness that is configured differently, e.g., such projections could be formed on straps of a flexible body harness wherein such straps are woven together with each other and/or with alignment straps in order to maintain the straps along respective trajectories at least partially around a body segment as described elsewhere herein.

A flexible body harness may additionally or alternatively be configured to limit an amount of shear that is applied, by elements of the flexible body harness, onto any one location of skin of a segment of a body to which the harness is mounted. This could be done, e.g., to reduce discomfort from use of the body harness or to reduce a risk of injury from use of the harness by specifying a maximum shear force and/or shear pressure that may be applied by, e.g., a strap of the flexible body harness. In some examples, this could be accomplished by coupling the straps of the body harness to a flexible underlayer of the body harness such that a strength of coupling between the straps and the flexible underlayer at one or more locations along the straps decreases when a shear between the strap(s) and the flexible underlayer at the particular location(s) increases beyond a specified maximum shear. For example, the straps of the body harness could be coupled to the underlayer by a layer of hook and loop fasteners that is unable to transmit shears above a maximum shear pressure or shear force (e.g., greater than a shear pressure corresponding to discomfort, e.g., a shear pressure greater than 2 pounds per square inch). Further, such configurations could facilitate evenly applying shears across straps of such a flexible body harness as regions of a strap of such a harness that are applying levels of shear above such a specified maximum shear could de-couple from the flexible underlayer, altering the trajectory of the strap such that the shear is applied more evenly across the strap. Further, the use of hook and loop fasteners could facilitate detection of regions of a strap that are exerting the greatest shear, e.g., by detecting a sound related to a 'micro-slip' of the hook-and-loop fasteners at a region that is exerting a large magnitude shear.

This is illustrated in FIG. 7C, which shows a flexible body harness 700c mounted to a segment of a body 705c (e.g., a calf). The flexible body harness 700c includes pairs of straps 720c that follow respective trajectories at least partially around the body segment 705c and that are coupled to a tether 710c and to a flexible underlayer 730c. The straps 720c are coupled to the flexible underlayer 730c such that a strength of coupling between the straps 720c and the flexible underlayer 730c at one or more locations along the straps 720c decreases when a shear between the strap(s) 730c and the flexible underlayer 730c at the particular location(s) increases beyond a specified maximum shear. In such a circumstance, the strap, at the particular location, could decouple from the underlayer and be displaced from an original trajectory 725c along which the strap exerted the shear, at a particular location, that is greater than the maximum shear and be displaced to a second trajectory 721c along which the strap could more evenly exert shears into skin of the body segment 705c.

B. Example Means for Distributing Applied Forces Between Pairs of Straps of a Harness A flexible body harness as described herein may include at least one pair of straps that are, when the described flexible body harness is mounted at least partially around a segment of a body, disposed along respective trajectories such that, when a force is applied to the straps via a tether of the flexible body harness, the straps apply a substantially even shear force and/or pressure to skin of the body segment across portions (e.g., across substantially all) of the straps. Such a flexible body harness may include one or more further tethers and associated straps to allow forces to be exerted on the body segment, via the flexible body harness, in respective different directions and/or from respective different locations on the body segment and/or flexible body harness.

In examples wherein more than one pair of straps is coupled to a particular tether of a flexible body harness, the flexible body harness could be configured to distribute a force applied to the particular tether amongst the pairs of straps of the harness in a variety of ways such that the force is distributed amongst the pairs of straps in a specified manner. For example, the flexible body harness could be configured such that a ratio of the forces applied, from the tether, to first and second pairs of straps is substantially equal to a specified ratio, e.g., related to relative lengths of the straps of the first and second pairs of straps. In some examples, the pairs of straps could be rigidly coupled to the tether and a compliance and/or geometry (e.g., a degree or pattern of branching of the tether) could be specified such that an applied force is distributed among the pairs of straps in the specified manner. Additionally or alternatively, the pairs of straps could be coupled to each other and/or to the tether in such a way that an applied force is distributed among the pairs of straps in the specified manner. This could include coupling the straps to each other and/or to the tether using pulleys and/or other coupling materials (e.g., loops of rigid or flexible material woven or otherwise disposed between pulleys and/or straps or other elements of a flexible body harness).

Figure 8:
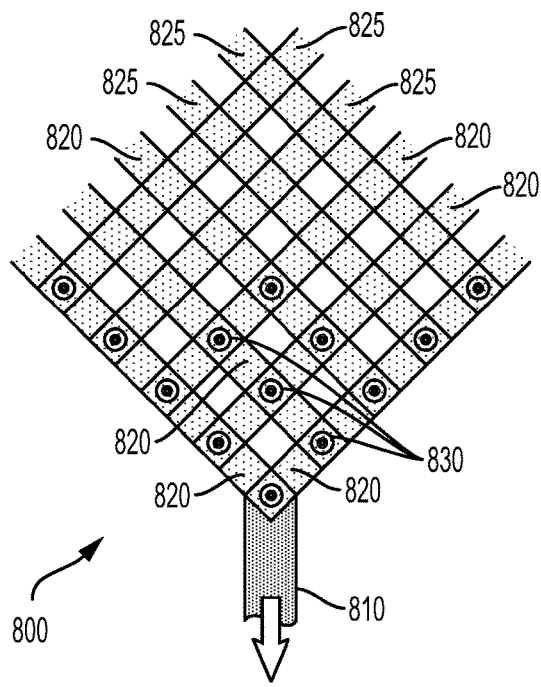
FIG. 8 illustrates the interconnection of straps of a body harness.

In a particular example, a flexible body harness could include a number of pairs of straps woven together and/or woven with a plurality of alignment straps such that forces applied to the harness via a tether of the harness are distributed between pairs of straps of the harness according to some specified distribution or pattern of forces (e.g., such that the forces are evenly distributed between each of the pairs of straps of the harness). Such a flexible body harness is shown in FIG. 8. The flexible body harness 800 includes pairs of load-bearing straps 820 that are woven together with alignment straps 825 and that are coupled to a tether 810. The load-bearing straps 820 are, when the harness 800 is mounted to a segment of a body, disposed along respective trajectories as described herein such that, when a force is applied to the flexible body harness 800 via the tether 810, a shear is applied to skin of the body segment, via the load-bearing straps 820, that is substantially even across respective portions of each of the load-bearing straps 820. As shown in FIG. 8, forces are coupled between the load-bearing straps 820 (and/or between the load-bearing straps 820 and the alignment straps 825) by brads 830. Alternatively, such straps may be coupled in some other way, e.g., by stitching, adhesives, or some other coupling means.

A pattern of weaving together of the load-bearing straps 820, a pattern of coupling of pairs of load-bearing 820 and/or alignment 825 straps by brads 830 (or other coupling means), a disposition of the locations of such couplings along the lengths of straps 820, 825 of the flexible body harness 800, or some other properties of the configuration of the flexible body harness 800 could be specified such that a force that is applied to the harness 800 via the tether 810 is distributed between pairs of load-bearing straps 820 of the harness 800 according to some specified consideration (e.g., such that the applied forces satisfy once or more specified ratios between pairs of pairs of load-bearing straps 820). Additionally or alternatively, a further strap or other material could be woven between the load-bearing straps 820 and/or between pulleys coupled to pairs of load-bearing straps 820 to provide such a specified distribution of forces between pairs of load-bearing straps 820 of the flexible body harness 800.

Additionally or alternatively, each pair of straps of a flexible body harness could be coupled to a tether of the harness via a load distributor. Such a load distributor could include one or more pulleys, loops or other configurations of load-bearing materials (e.g., ropes, cables, strings, chains), or other elements configured to transmit forces between the pairs of straps and the tether according to a specified pattern of distribution of such forces between the pairs of straps. For example, a load distributor could be configured to distribute an applied force equally between pairs of straps of the flexible body harness. In another example, the load distributor could be configured to distribute an applied force between pairs of straps of the flexible body harness according to a set of ratios of forces between the pairs of straps, e.g., a set of ratios corresponding to a ratio of the lengths of the straps in each pair such that a level of shear force and/or shear pressure applied to skin of a body segment by straps of each pair of straps is substantially the same across all of the straps of the body harness.

Figure 9A:
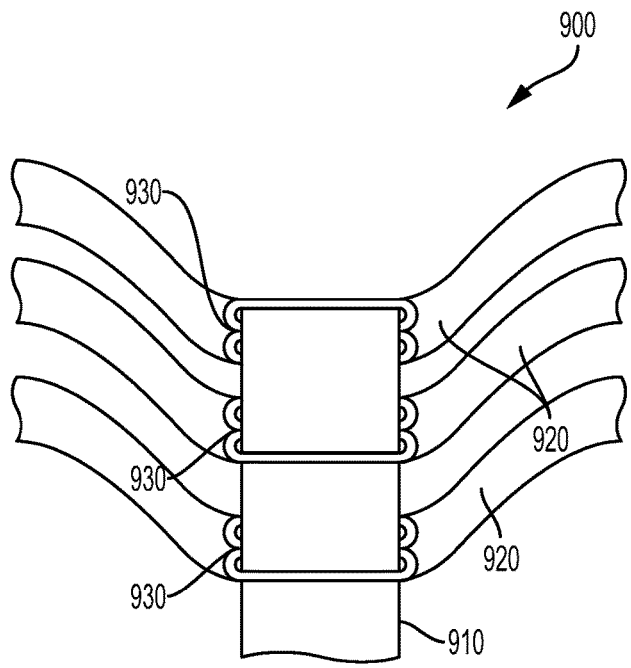
FIG. 9A illustrates the interconnection of straps of a body harness.

Such a flexible body harness is shown in FIG. 9A. The flexible body harness 900 includes pairs of load-bearing straps 920 that each coupled to a respective pulley 930. The pulleys 930 form part of a load distributor that also includes a continuous loop of load-bearing material 910 (e.g., a rope, a chain, a cable, a tether) that is, in turn, coupled, via another pulley, to a tether of the body harness 900 via which a force may be applied to the body harness 900. The pulleys 930 are, in the illustrated example, configured as figure-eight clips, with the corresponding pair of straps coupled to/through a first opening of the figure-eight clip and the load-bearing loop 910 coupled to/passing through a second opening of the figure-eight clip. Other forms of pulley, and method of coupling straps, loops of load-bearing material, or other elements of a load distributor and/or flexible body harness to such pulleys could also be used.

Figure 9B:
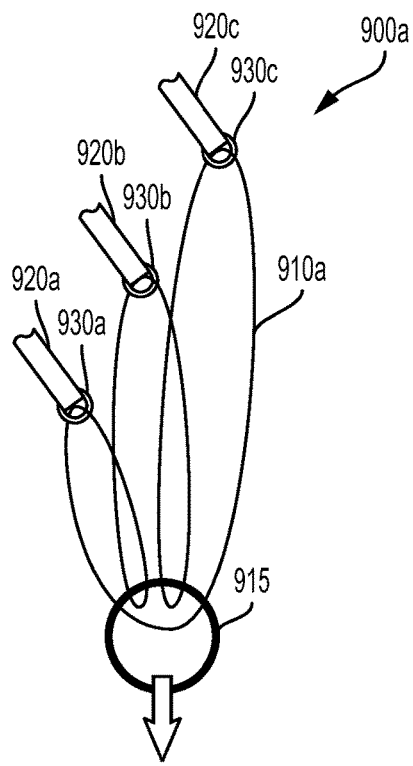
FIG. 9B illustrates a schematic of a first configuration of interconnection of the straps of the body harness illustrated in FIG. 9A.

The continuous loop of load-bearing material 910 could be woven through or otherwise coupled to the pulleys 930 and/or to a tether (e.g., to through a pulley coupled to a tether) in a variety of ways in order to facilitate distribution of forces between pairs of straps of the body harness 900 according to some specified distribution of such forces. An example is shown schematically in FIG. 9B. FIG. 9B shows each of the pairs of straps 920a, 920b, 920c coupled to a respective pulley 930a, 930b, 930c. FIG. 9B also shows a tether pulley 915 that is coupled to a tether of the flexible body harness 900. A pattern of connection between the pulleys 930a, 930b, 930c, 915 by a first example continuous loop of load-bearing material 910a is also shown. The first example continuous loop of load-bearing material 910a loops from the tether pulley 915 through each of the strap pulleys 930a, 930b, 930c and back to the tether pulley 915 in turn such that forces from the tether (via the tether pulley 915) may be evenly distributed to each of the pairs of straps 920a, 920b 920c. Note that such a distribution of forces could be achieved in other ways, e.g., by passing a continuous loop of load-bearing material through the illustrated pulleys multiple times each (e.g., to increase an amount of force that can be distributed by the load distributor), by including multiple continuous loops of load bearing material passing thought the same pulleys, through further pulleys coupled to the pairs of straps and tether, or according to some other scheme (e.g., to increase an amount of force that can be distributed by the load distributor and/or to provide redundancy), or according to some other configuration.

Figure 9C:
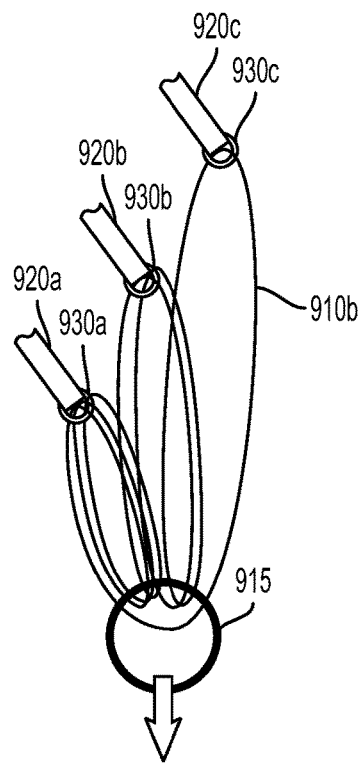
FIG. 9C illustrates a schematic of a second configuration of interconnection of the straps of the body harness illustrated in FIG. 9A.

In another example, the continuous loop of load-bearing material 910 could pass through each pulley 930a, 930b, 930c a respective number of times, such that a ratio between the forces distributed to each of the pairs of straps 920a, 920b, 920c may be specified related to the relative number of times the continuous loop of load-bearing material 910 loops through each of the pulleys 930a, 930b, 930. An example is shown schematically in FIG. 9C. FIG. 9C shows each of the pairs of straps 920a, 920b, 920c coupled to a respective pulley 930a, 930b, 930c. FIG. 9C also shows a tether pulley 915 that is coupled to a tether of the flexible body harness 900. A pattern of connection between the pulleys 930a, 930b, 930c, 915 by a second example continuous loop of load-bearing material 910c is also shown. The second example continuous loop of load-bearing material 910b loops from the tether pulley 915 through the first strap pulley 930a and back to the tether pulley 915 three times, through the second strap pulley 930b and back to the tether pulley 915 two times, and through the third strap pulley 930c and back to the tether pulley 915 once. As such, half of forces from the tether (via the tether pulley 915) may be distributed to the first pair of straps 920a, one third of forces from the tether may be distributed to the second pair of straps 920*b*, and one sixth of forces from the tether may be distributed to the third pair of straps 920*c*.

Other patterns of passage of a continuous loop of load-bearing material of a load distributor may be used to distribute forces between pairs of straps of a flexible body harness according to a different ratio of forces. Further, such a load distributor may include multiple continuous loops of load-bearing material coupled to respective sets of pairs of straps (and associated pulley or other coupling means) and/or to further tether pulleys or other pulleys according to some other configuration. For example, a first set of pairs of straps could be coupled together, via a first continuous loop of load-bearing material and associated pulleys, to a first pulley block and a second set of pairs of straps could be coupled together, via a second continuous loop of load-bearing material and associated pulleys, to a second pulley block. The first and second pulley block could be coupled together, via a third continuous loop of load-bearing material and associated pulleys, to a tether. Such a system could be configured to distribute forces from the tether between the first and second pulley blocks, and from each of the first and second pulley blocks between pairs of pulleys within each respective set of pairs of pulley, according to some specified pattern of distribution of forces between pairs of straps of the first and second sets of pairs of straps. Other configurations of a load distributor of a flexible body harness could be used.

C. Example Methods for Adjusting a Trajectory of a Strap of a Harness to Evenly Distribute Forces Applied by the Strap Along the Length of the Strap Trajectories of straps of flexible body harnesses as described herein could be determined based on a model of a body segment to which the body harness is to be mounted (e.g., based on a cylindrical geometry, based on a measured geometry of a body segment of a particular wearer, based on a calculated average geometry of a body segment of a population of individuals). Additionally or alternatively, the flexible body harness could be adjustable such that the trajectory of one or more straps of the harness can be adjusted, e.g., to increase a degree to which forces exerted by the strap into skin are evenly distributed across one or more portions of the strap. A force could be applied to such a flexible body harness, when the flexible body harness is mounted to a body segment, and the resulting pattern of shear applied, from the straps to skin of the body segment, could be determined. Based on this determined pattern of shear, the trajectory of one or more of the straps could be adjusted to more evenly distribute the shear applied by the adjusted strap to skin of the body segment to which the body harness is mounted. This could include determining a location, along a strap, at which the applied shear is the greatest and adjusting the strap at the determined location such that the shear applied to skin of the body segment, via the strap at the determined location is reduced. Such a process could be performed multiple times (e.g., iteratively) to optimize the trajectory of a strap of the flexible body harness.

The shear exerted by a strap of a flexible body harness, at a particular location along the strap, onto skin of a body segment to which the body harness is mounted could be determined in a variety of ways. The shear applied by the strap at one or more locations could be determined based on sensor outputs, e.g., based on the outputs of pressure, force, and/or strain sensors disposed on or within the straps, on the surface of the skin of a body segment, on or within a flexible underlayer of the body harness, or disposed on or within some other element(s) of the body harness and/or of the body segment to which the harness is mounted. Additionally or alternatively, index markings (e.g., regularly spaced lines or dots, a regularly spaced grid) could be formed and/or disposed on the straps, flexible underlayer, or other element(s) of the body harness (e.g., as a deposited pigment, as differently-colored strands in a fabric of element(s) of the harness) and a deformation of such index markings could be used to determine the relative or absolute shear applied by the strap at one or more locations.

Figure 10A:
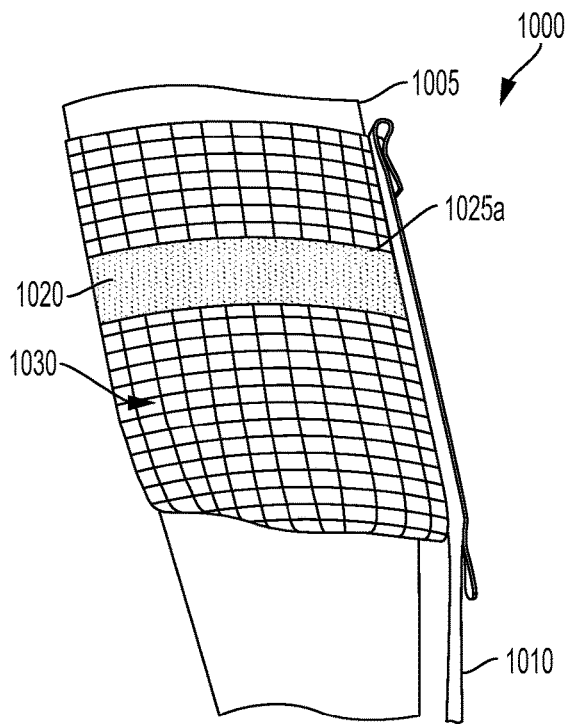
FIG. 10A is a side view of a body harness that is mounted around a calf of a body.

An example of such a process to adjust the trajectory of a strap of a flexible body harness is illustrated in FIGS. 10A-10D. FIG. 10A shows a flexible body harness 1000 mounted to a segment of a body 1005 (e.g., a calf). The flexible body harness 1000 includes a strap 1020 that follows a first trajectory 1025*a* at least partially around the body segment 1005 and that is coupled to a tether 1010 and to a flexible underlayer 1030. As shown, the flexible underlayer 1030 includes a grid of index markings 1030 (e.g., formed from pigment deposited on the material of the underlayer 1030, formed from differently-colored strands of material woven into a fabric of the underlayer 1030, formed from a texture of the weave of the underlayer 1030) that can be observed to determine an absolute or relative amount and distribution of shears (or other forces or pressures) applied to the underlayer 1030 and/or to skin of the body segment 1005 (e.g., by determining an absolute or relative amount of deformation of the grid of index markings) when a force is applied to the flexible body harness 1000 via the tether 1010.

Figure 10B:
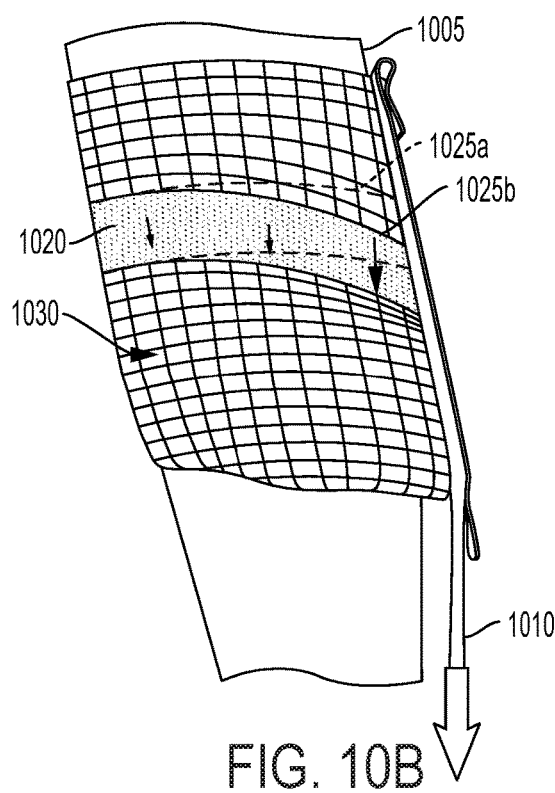
FIG. 10B is a side view of the body harness shown in FIG. 10A after applying a force to the body harness.

FIG. 10B shows the flexible body harness 1000 of FIG. 10A after a force (illustrated by the arrow) has been applied to the flexible body harness 1000 via the tether 1010. As a result, the trajectory of the strap 1020 now follows a second trajectory 1025*b* (the original trajectory 1025*a* is illustrated, in FIG. 10B, by dashed lines for comparison). Further, the shear applied by the strap 1020 to the skin via the underlayer 1030 is not evenly distributed across the strap (illustrated by the unequally-sized arrows on the strap 1020). This results in an uneven deformation of the index of grid lines on the flexible underlayer 1030, which can be observed and used to determine a location on the strap at which the strap is applying the greatest shear. Some other method or means (e.g., a pressure, force, and/or strain sensor) could be used to determine such a location of greatest applied shear and/or to determine the shear applied by the strap 1020 at a number of different locations. As illustrated in FIG. 10B, this location of greatest applied shear is located proximate to the tether 1010.

Figure 10C:
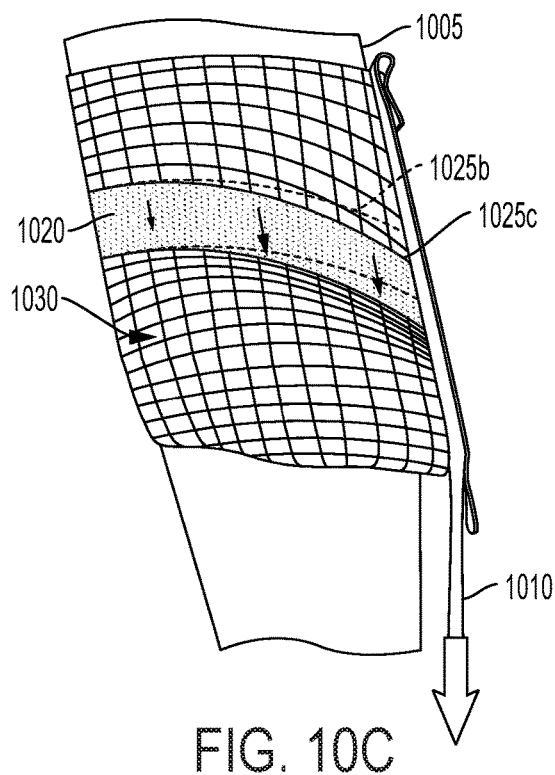
FIG. 10C is a side view of the body harness shown in FIG. 10B after adjusting a strap of the body harness.

The strap 1020 could be adjusted at the determined location of greatest applied shear such that the amount of shear applied at the determined location is reduced. Such a reduction could further act to even out the distribution of application of shear (e.g., to even out the application of shear force and/or shear pressure), by the strap 1020 onto skin of the body segment 1005 via the underlayer 1030, across the strap 1020. The result of such an adjustment is shown in FIG. 10C. As a result, the trajectory of the strap 1020 now follows a third trajectory 1025*c* (the second trajectory 1025*b* is illustrated, in FIG. 10C, by dashed lines for comparison). Further, the shear applied by the strap 1020 to the skin via the underlayer 1030 is now more evenly distributed across the strap, with the shear applied at the location of the adjustment having been reduced from the shear illustrated in FIG. 10B (illustrated by the unequally-sized arrows on the strap 1020). This results in a new uneven deformation of the index of grid lines on the flexible underlayer 1030 across the length of the strap 1020. A new location of greatest applied shear could be determined and the strap adjusted at that determined location to more evenly distribute the shear applied by the strap 1020 across the length of the strap 1020.

As illustrated in FIG. 10C, this new location of greatest applied shear is located in the middle of the strap 1020.

Figure 10D:
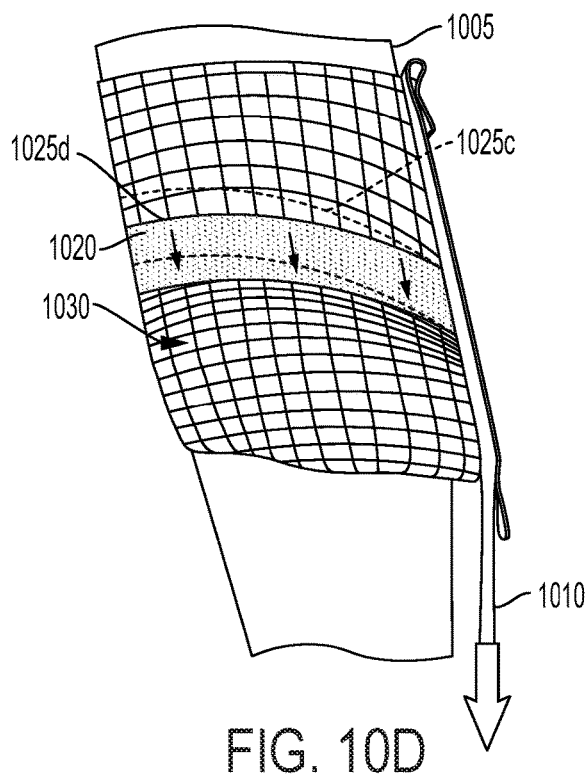
FIG. 10D is a side view of the body harness shown in FIG. 10C after further adjusting the strap of the body harness.

The result of such a further adjustment is shown in FIG. 10D. As a result of this further adjustment, the trajectory of the strap 1020 now follows a fourth trajectory 1025d (the third trajectory 1025c is illustrated, in FIG. 10C, by dashed lines for comparison). Further, the shear applied by the strap 1020 to the skin via the underlayer 1030 is now more evenly distributed across the strap, with the shear applied at the location of the adjustment having been reduced from the shear illustrated in FIG. 10B (illustrated by the substantially equally-sized arrows on the strap 1020). This results in a new, substantially even deformation of the index of grid lines on the flexible underlayer 1030 across the length of the strap 1020.

Note that the flexible body harness 1000, and the process of adjusting the trajectory of a strap of such a flexible body harness based on determined shears applied by the strap, illustrated in FIGS. 10A-10D are intended as non-limiting illustrative examples of embodiments of such harnesses and/or processes. A flexible body harness could include more or fewer straps and/or pair of straps or other additional or alternative element(s). Further, a process for adjusting trajectories of such straps could be performed to adjust the trajectories of each strap or pair of straps of such a body harness sequentially (e.g., by fully adjusting the trajectory of each strap in turn), simultaneously (e.g., by applying small adjustments to each of the straps in turn, repeating the sequence of adjustment multiple times), or according to some other scheme. Other methods of adjusting the trajectory of straps of a flexible body harness as described herein are anticipated by the inventors.

III. Example Body Augmentation System

A flexible body harness, as described herein, may be employed in a variety of applications (e.g., as part of a variety of systems or devices) to transmit forces into segments of a body via skin of the surface of such a body segment. Such flexible body harnesses could be used to apply forces to segments of a human body as part of a rehabilitative or prosthetic device, a strength augmentation device, a training device, or some other system or device wherein the ability to evenly, safely, and comfortably transmit forces into a body segment of a human or animal body may be advantageous. In particular, a flexible exosuit configured to be worn by a person and to provide forces between different body segments of the person and/or between body segments of the person and a tool, pack, prosthetic limb, or other object may include one or more such flexible body harnesses to facilitate applications of the flexible exosuit. A flexible body harness of such a flexible exosuit may be configured to apply forces to a particular body segment of a wearer in one or more directions from one or more locations (e.g., via one or more tethers and associated pairs of straps of the particular flexible body harness).

Such a flexible exosuit may be configured in a variety of ways according to a variety of applications. Indeed, it is this versatility in the choice of elements (e.g., number, type, and location of mounting of flexible body harnesses and actuators coupled thereto) and software that establishes such a flexible exosuit as a human augmentation platform for such a variety of applications. A flexible exosuit may be configured to apply forces to segments of the lower body, upper body, torso, or combinations of some or all of these parts of a wearer. A flexible exosuit could be symmetric (able to apply the same types of forces and torques to one side of a wearer's body as to the opposite side) or could be asymmetric (e.g., to enable strength assists and/or rehabilitation to a wearer that has experienced an injury to one limb and not to the opposite limb). Different overall topologies of configuration of flexible exosuits may correspond to and/or be specified by respective applications of flexible exosuits.

Figure 11C:
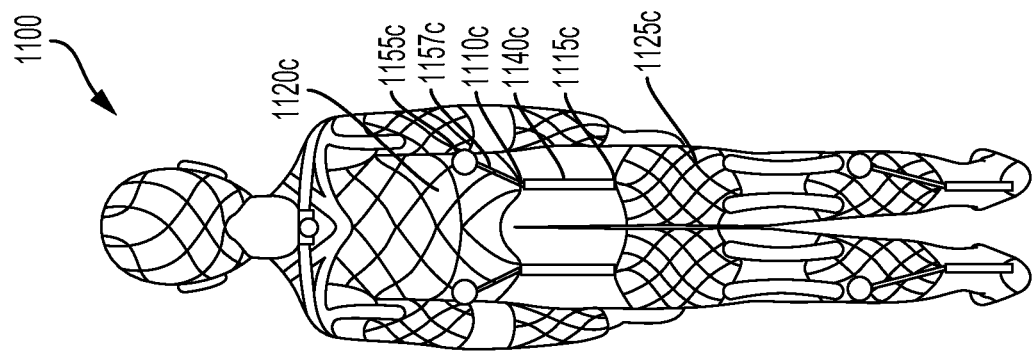
FIG. 11C is a back view of the example flexible exosuit of FIG. 11A.
Figure 11B:
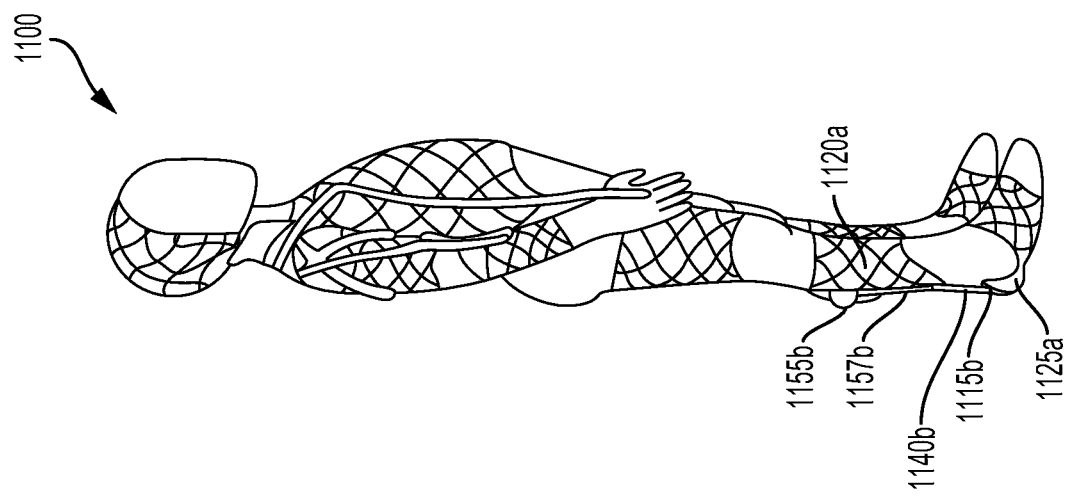
FIG. 11B is a side view of the example flexible exosuit of FIG. 11A
Figure 11A:
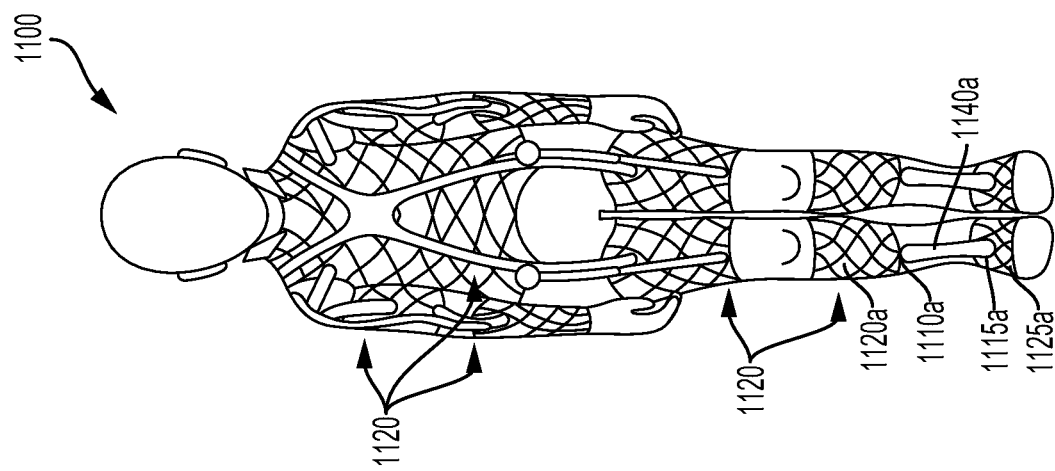
FIG. 11A is a front view of an example flexible exosuit that includes a number of body harnesses.

FIGS. 11A, 11B, and 11C show side, front, and back views, respectively, of a flexible exosuit 1100 being worn by a wearer on the wearer's torso, head, and limbs. The flexible exosuit includes a number of flexible body harnesses 1120 as described herein mounted to respective segments of the wearer's body. Further, the flexible exosuit 1100 includes a number of active and/or passive force-transmitting elements configured to apply forces between segments of the wearer's body via flexible body harnesses 1120 of the flexible exosuit 1100 to which the force-transmitting elements are coupled. Such force-transmitting elements may include flexible linear actuators (e.g., twisted string actuators (TSAs)), clutched-compliance elements (e.g., flexible electrostatic clutching elements), or other active or passive force-transmitting elements. The clutched-compliance elements could be configured to enable switching between different levels of compliance and/or to enable the storage and later release of mechanical energy.

The flexible exosuit 1100 is configured to apply forces to the segments of the wearer's body and/or to loads, tools, prosthetic limbs, or other objects to facilitate one or more activities of the wearer. For example, flexible exosuit 1100 could be operated to assist the wearer in walking by adding energy to the motion of the wearer's legs and/or by selectively extracting energy from the wearer's legs during one phase of locomotion and injecting a portion of the extracted energy to assist the motion of the wearer's legs during another phase of activity. In another example, the flexible exosuit could additionally or alternatively enable the wearer to carry loads heavier than the wearer would be capable of carrying on his/her own and/or carrying loads farther than the wearer would be capable on his/her own. Other activities of the wearer could be facilitated by the flexible exosuit 1100. Additionally or alternatively, the flexible exosuit 1100 could be configured and/or operated to perform other functions.

The flexible exosuit 1100 includes a multitude of elements to enable the functions described herein. In particular, the illustrated example flexible exosuit includes a passive elastic shock-absorbing force-transmitting element 1140a coupled to first 1120a and second 1125a flexible body harnesses via respective first 1110a and second 1115a tethers. The first 1120a and second 1125a flexible body harnesses are mounted to, and configured to evenly apply force via the skin of, the calf and foot of the wearer, respectively. As such, the passive elastic shock-absorbing force-transmitting element 1140a is able to exert a force between the calf and foot of the wearer and/or to exert a flexing torque on the ankle of the wearer. The illustrated example flexible exosuit additionally includes first 1140b and second 1140c active force-transmitting elements. The first active force-transmitting element 1140b is coupled to the first 1120a and second 1125a flexible body harnesses via respective third 1110b and fourth 1115b tethers. As such, the first active force-transmitting element 1140b is able to exert a force between the calf and foot of the wearer and/or to exert an extending torque on the ankle of the wearer The flexible exosuit 1100 further includes a second active force-transmitting element 1140c coupled to third 1120c and fourth 1125c flexible body harnesses via respective fifth 1110c and sixth 1115c tethers. The third 1120c and fourth 1125c flexible body harnesses are mounted to, and configured to evenly apply force via the skin of, the torso and thigh of the wearer, respectively. As such, the second active force-transmitting element 1140c is able to exert a force between the torso and thigh of the wearer and/or to exert an extending torque on the hip and/or back of the wearer.

The first 1120b and second 1120c active force-transmitting elements are coupled, via respective transmissions 1157b, 1157c, to respective actuators 1155b, 1155c. The actuators may include electrical motors, hydraulic cylinders, solenoids, reduction gears, clutches, or other elements configured to generate a linear or rotary force that may be applied, via the transmission and force-transmitting elements, to flexible body harnesses of the flexible exosuit 1100. Such active force-transmitting elements and associated elements may be configured as twisted string actuators.

Twisted string actuators are flexible structures capable of generating forces along their length. A twisted string actuator includes at least two flexible 'strands' (e.g., wires, cables, ropes, fibers) twisted about each other (in cases where there are two strings, the two strings can be referred to as a "twisted pair"). In some examples, a first end of a twisted string is attached to a first actuated element, and a second end of the twisted string, opposite the first end, is attached to a second actuated element such that the location of the second end does not translate relative to the second actuated element and such that the second end can be rotated by a rotational actuator, e.g., an electric motor 160. The twisted string actuator transduces a rotation or torque applied to the second end of the twisted string into a displacement or force, respectively, between the first and second actuated elements. Properties of a twisted string (e.g., compliance, twist pitch, diameter, length) and the driving rotational actuator (e.g., acceleration, speed, torque, rotational inertia) can be chosen to produce a twisted string actuator having one or more properties according to an application, for example, a high rate of change of displacement, a high transmission ratio between the rotational actuator and the forces applied between the first and second actuated elements, a certain compliance, or other properties. Further, a twisted string can be flexible and can be implemented in a curved configuration. For example, the twisted string could be housed in a stiff tube (similar to a Bowden cable, where the twisted string and the stiff tube are analogous to the inner cable and the outer housing, respectively) wrapped around a joint of the wearer, with each end of the twisted string attached as described above to a respective actuated element on either side of the joint. Such a twisted string actuator could be operated to apply forces between the first and second actuated elements across the joint; further, the flexibility of the twisted string and the stiff tube can allow the twisted string actuator to remain proximate to a surface of the wearer as the joint moves or as other aspects of the flexible exosuit 1100 or wearer change configuration. Note that a twisted string actuator can have more than two flexible strings, be connected to actuated elements in different ways, be driven by other or multiple rotational actuators, or be configured differently to these examples in other ways.

Force-transmitting elements of a flexible exosuit (e.g., force-transmitting element coupled between two or more flexible body harnesses of such a flexible exosuit) may include exotendons. Exotendons are structures capable of transmitting forces along their length and capable of having one or more mechanical properties (e.g., a compliance) controlled by an electrical or other signal. Exotendons can be flexible or rigid. Exotendons can be thin, flexible, and conformal to a curved or flat surface. For example, an exotendon could include an electrostatic clutch (or some other type of mechanical clutch) connected in series with a component having a specified compliance (e.g., a spring). The clutch itself could have a first compliance when inactive (possibly a very high compliance, corresponding to an effectively nearly complete mechanical decoupling between the ends of the clutch) and a second compliance when active (possibly a very low compliance, corresponding to the compliance of individual components of the clutch due to an effectively non-compliant mechanical coupling between the ends of the clutch). Thus, exotendons could be considered a type of clutched-compliance element. The clutch and specified-compliance component could be discrete, or could be interdigitated, intercalated, or otherwise assembled proximately to form an exotendon. Further, an exotendon could contain multiple specified-compliance elements, independently or commonly-controlled clutches, or other elements. In some examples, the overall compliance of an exotendon could be controlled to a variety of discrete or continuous levels by controlling multiple clutches. In some examples, an exotendon could be operated to store a mechanical energy, e.g. by engaging a clutch to prevent relaxation of a stretched specified-compliance element, and to later release the stored mechanical energy. Other configurations and methods of operating an exotendon are described herein.

A flexible exosuit (e.g., 1100) could include additional wholly or partially flexible linear actuators (i.e., actuators capable of being operated to produce a linear force and/or displacement and that are wholly or partially flexible) and/or other varieties of wholly or partially flexible actuators. In some examples, the flexible exosuit 1100 could include actuators that include electroactive polymer artificial muscle (EPAM). EPAM actuators change size or shape in response to an applied electrical field. Conversely, a size or shape change in an EPAM actuator caused by an external force can cause an electric field to develop in or on the EPAM actuator. An EPAM actuator can include two or more electrodes configured to interact (by way of an electric field) with an electroactive polymer material. The electroactive polymer material could include dielectric, ferroelectric, electrostrictive, or other electrically-active molecules, crystals, or materials embedded in a polymer such that application of an electric field causes the electrically-active materials to orient, expand, contract, or otherwise respond to the electric field to cause the electroactive material to change a size or shape. For example, the electroactive polymer material could be composed of an elastic dielectric configured to experience electrostatic compression. The electroactive material and electrodes can be configured in a variety of ways to enable a desired relationship between mechanical deformation of the EPAM and an electric field between the electrodes. In some examples, the material and electrodes could be configured such that the EPAM actuator transduced an electric field into a size change in one direction, such that the EPAM actuator could be operated as a flexible linear actuator. EPAM actuators could additionally or alternatively be used to generate electrical energy from mechanical energy. In some examples, the flexible exosuit 1100 could include actuators that drive and/or apply a tension to a cable or cables. For example, the flexible exosuit could include a linear pull solenoid attached to a cable. The linear pull solenoid could be attached to a first actuated element and the end of the cable opposite the end of the cable attached to the solenoid could be attached to a second actuated element. Application of an electrical current to the solenoid could result in a force applied between and/or a displacement of the first and second actuated elements. Other wholly or partially flexible actuators of the flexible exosuit are anticipated by the inventors.

A flexible exosuit 1100 could include composite actuators; that is, wholly or partially flexible assemblies mechanically connected between a first actuated element and a second actuated element and including at least one actuator. For example, the flexible exosuit 1100 could include a smart tendon exomuscle (STEM) actuator that includes a linear actuator and at least one clutched compliance element (that is, an element that includes a mechanical clutch mechanically coupled in series with a component having a specified compliance). The linear actuator could be a twisted string actuator. The clutched compliance element could be configured similarly to an exotendon as described herein. A STEM could include a single twisted string actuator connected to the first actuated element and mechanically coupled in series with an exotendon connected to the second actuated element. A STEM could include an exotendon connected between the first and second actuated elements and connected in parallel with a single twisted string actuator connected to the first actuated element and mechanically coupled in series with an exotendon connected to the second actuated element. A STEM could include a single twisted string actuator connected to the first actuated element and mechanically coupled in series with an exotendon also connected to the first actuated element. A STEM could be configured to have a topology and/or properties inspired by biological actuators, e.g., muscles and tendons, and could further be operated to mimic the operation of biological actuators. Other configurations of a STEM are anticipated by the inventors. A STEM could be operated to extract, store, inject, or otherwise transduce mechanical forces and energies to and from a wearer of the flexible exosuit 1100 and/or between elements of the flexible exosuit.

The flexible exosuit 1100 could additionally include an undersuit configured to maintain the location of elements of the flexible exosuit 1100 relative to elements of the body of the wearer. The undersuit could include or be continuous with a flexible underlayer of one or more of the flexible body harnesses 1120 of the flexible exosuit 1100. The undersuit could be composed of a variety of flexible fabrics, textiles, or other materials and could enable a variety of functions of the flexible exosuit 1100. For example, the undersuit could include high-strength materials to protect the wearer from projectiles, fabrics to manage moisture emitted by the skin of the wearer, or other materials.

The flexible exosuit 1100 includes additional elements. The flexible exosuit 1100 includes one or more controllers configured to operate the flexible exosuit 1100. The controller(s) could be configured to receive data from a plurality of sensors in the flexible exosuit 1100, generate commands to operate actuators (e.g., 1155a, 1155b) of the flexible exosuit 1100, and to perform other functions. The controller(s) could be configured to operate communications elements in the flexible exosuit 1100, for example, Bluetooth radios, WiFi radios, LTE or other cellular radios, near-field RF communications devices, modems, or other communications devices. The controller(s) could be configured to operate such communications devices to receive commands, send telemetry, enable communications between the wearer and some other person or system, or enable some other function. The controller(s) could be configured to operate one or more user interfaces (UIs) in the flexible exosuit 1100 and/or in systems in communication with the flexible exosuit 1100. For example, the controller(s) could operate a touch screen disposed on or in a sleeve worn by the wearer to present information about the operation of the flexible exosuit 1100 to the wearer and/or to receive commands from the wearer, e.g., commands to alter the functioning of the flexible exosuit 1100. UIs in the flexible exosuit 1100 could include displays, touchscreens, touchpads, buttons, sliders, knobs, indicator lights, speakers, headphones, microphone, or other elements.

The controller(s) could additionally or alternatively be configured to send and/or receive commands from the wearer using sensors and/or actuators of the flexible exosuit 1100. In some examples, the controller(s) could be configured to use sensors disposed in the flexible exosuit 1100 to detect command gestures performed by the wearer and to alter the functioning of the flexible exosuit 1100 based on those command gestures. In some examples, the controller(s) could use actuators or other elements of the flexible exosuit 1100 to provide feedback to the wearer, to indicate a state of the flexible exosuit 1100 to the wearer, and/or to provide some other information to the wearer. For example, the controller(s) could produce a pulse or sequence of pulses using twisted string actuator to indicate that the wearer should adopt a more crouched posture. In another example, the flexible exosuit 1100 could include one or more vibrating, heating, or electrostimulating elements, and the controller(s) could operate the vibrating, heating, or electrostimulating elements to indicate a state of the flexible exosuit 1100 to the wearer, and/or to provide some other information to the wearer. Other methods of using elements of the flexible exosuit 1100 to indicate information to the wearer are anticipated by the inventors.

The flexible exosuit 1100 may include a plurality of sensors configured to detect information about the operation and status of the flexible exosuit 1100, the wearer, and/or an environment of the wearer. These sensors include but are not limited to force sensors (e.g., load cells), strain or displacement sensors (e.g., capacitive sensors, laser or ultrasonic rangefinders, linear encoders, rotary encoders on rotary elements of rotary-to-linear transducers or transmissions), angle sensors (e.g., magnets and magnetometers, filtered accelerometers, magnetometers, and/or gyroscopes), location, velocity, and/or acceleration sensors (e.g., GPS receivers, filtered or unfiltered accelerometers, magnetometers, and/or gyroscopes), temperature sensors, EMG sensors, ECG sensors, pulse sensors, blood pressure sensors, galvanic skin response sensors, humidity sensors, chemical sensors (e.g., $CO_2$, CO, $O_2$ sensors), ionizing radiation sensors, cameras, SONAR, LIDAR, proximity sensors, or other sensors. The sensors can be discrete or the sensors can be part of an actuator or other element of the flexible exosuit 1100. For example, an exotendon could be configured to be used to detect one or more properties of the exotendon or the environment of the exotendon (e.g., to detect a strain and/or force experienced by the exotendon by measuring an impedance or voltage between and/or current through a pair of electrodes of the exotendon).

The sensors can be operated to generate data that can be used to operate the flexible exosuit 1100. Data generated by the sensors could be used by a controller included in the flexible exosuit 1100 to operate actuators (e.g., 1155a, 1155b) to perform some function. For example, the sensors could generate data indicating that the wearer was engaging in locomotion and that the wearer was at a first specified phase of a stereotypical locomotor cycle, and the controller could use that data to operate exotendons to extract negative work from the wearer. At a later point in time, the sensors could generate data indicating that the wearer was engaging in locomotion and that the wearer was at a second specified phase of the stereotypical locomotor cycle, and the controller could use that data to operate the exotendons to assist the locomotion of the wearer by transferring energy to the leg of the wearer and/or to operate the twisted string actuators 1155a, 1155b to transfer energy to the leg of the wearer.

A flexible exosuit could be configured to apply forces and/or torques at a single joint or right/left pair of joints of a wearer. Such a flexible exosuit could include elements covering/disposed proximate to parts of the wearer distant from the single joint or could only include elements covering/disposed proximate to the single joint. Elements of the flexible exosuit configured to apply forces/torques to the single joint could be disposed proximate to the single joint or could be disposed elsewhere and mechanically coupled to the single joint, e.g., through a belt, cable, gears, twisted-string transmission, and/or some other method. In some examples, a flexible exosuit could be configured to apply forces across the ankles of a wearer. For example, the flexible exosuit could include a smart tendon exomuscle disposed on the back of the wearer's leg and configured to apply and/or transmit forces between two actuated elements mechanically coupled to the wearer's calf and foot, respectively. Elements of the STEM (e.g., a motor configured to drive a twisted string transmission) could be disposed near the ankle (e.g., on the back of the calf) or at other locations (e.g., attached to a belt worn by the wearer, and mechanically coupled to the ankle by a twisted string or cable transmission). Such a flexible exosuit could include additional elements, e.g., batteries, controllers, sensors, disposed according to an application. For example, sensors of the flexible exosuit could be disposed across the leg and torso to enable gait detection, a battery powering the flexible exosuit could be located on a belt worn by the wearer, etc.

A flexible exosuit could be operated in combination with some other prosthetic system. For example, a wearer could be missing a limb, and the flexible exosuit could operate in combination with a prosthetic worn by the wearer and configured to replace some of the function of the missing limb. The flexible exosuit could be integrated with the prosthetic, and could be configured to mount the prosthetic to the wearer and/or to transmit forces and/or torques between the prosthetic and the wearer. In some example, information detected using sensors and/or actuators of the flexible exosuit (e.g., information about the posture and movement of a leg of the wearer) could be used to operate the prosthetic (e.g., a detected locomotor gait type, phase, speed, or other information from the leg of the wearer could be used to control a leg prosthetic to assume a configuration complementary to the configuration of the wearer's leg). Such a flexible exosuit could additionally be operated to optimize the movements of the wearer to complement the operation of the prosthetic during an activity (e.g., altering a gait pattern of a wearer's leg to complement a pattern of operation of a leg prosthetic).

The illustrations of elements of a flexible exosuit in FIGS. 11A-C are intended as examples. A flexible exosuit could include actuators in a similar or different arrangement according to an application. In some examples, elements of a flexible exosuit could allow the arms and legs of the body of a wearer to be controllably mechanically coupled. For example, exotendons could be disposed in an exosuit to couple motions of the arms of a wearer to motions of the legs of a wearer. This configuration could enable a wearer to use the wearer's arms to assists the wearer's legs in walking, running, sprinting, climbing, or some other activity. Other alternate configurations and applications of a flexible exosuit are anticipated by the inventors. Additionally, illustrated twisted string actuators and exotendons are meant as illustrative examples of actuators. Additionally or alternatively, twisted string actuators, exotendons, EPAMs, STEMs, motor-and-drum-driven cables, servos, pneumatic or hydraulic pistons, racks and pinions, motorized screw drives or ball screws, or other actuators could be used in place of the illustrated twisted string actuators or exotendons according to an application.

Figure 12A:
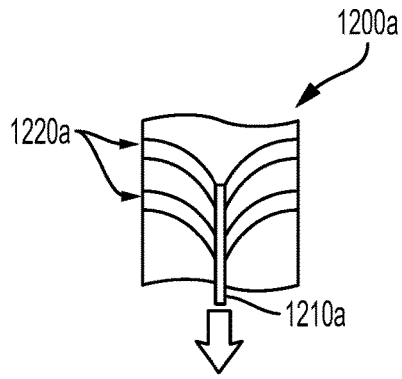
FIG. 12A is a schematic of elements of a body harness.

A flexible body harness as described herein (e.g., a flexible body harness that is part of a flexible exosuit, e.g., 1100) may be configured as described herein in a variety of ways to receive forces via one or more tethers, from one or more directions at one or more locations, and to apply such forces evenly across skin of a segment of a body as normal and/or shear stresses. In some examples, such a flexible body harness may include a single tether configured to apply forces from a single direction (e.g., along a long axis of the body segment, in a proximal anatomical direction or in a distal anatomical direction), at a single location, relative to a body segment to which the flexible body harness is mounted. This is illustrated by way of example in FIG. 12A, which illustrates an example flexible body harness 1200a. The flexible body harness 1200a includes a single tether 1210a via which forces may be applied to the flexible body harness 1200a. A set of pairs of straps 1220a are coupled to the tether and optionally to other elements of the flexible body harness 1200a (e.g., a flexible underlayer of the flexible body harness 1200a). When the set of pairs of straps 1220a is mounted to a body segment and force is applied via the tether, the set of pairs of straps 1220a may be disposed along respective trajectories at least partially enclosing the body segment such that shear is evenly applied across the straps 1220a into skin of the body segment.

Alternatively, a flexible body harness may include multiple tethers. For example, a flexible body harness could include two tethers configured to allow forces to be applied to a body segment in two different directions, e.g., a first direction in an anatomically distal direction relative to the body segment and in a second direction in an anatomically proximal direction relative to the body segment. Further, the locations at which such forces are applied, via respective tethers, may be proximate. This is illustrated by way of example in FIG. 12B, which illustrates an example flexible body harness 1200b. The flexible body harness 1200b includes first 1210b and second 1215b tethers via which forces may be applied to the flexible body harness 1200b. Due to the location of the tethers 1210b, 1215b, such forces may be applied to the flexible body harness 1200b at proximate locations. Two sets of pairs of straps 1220b, 1225b are each coupled to a respective tether 1210b, 1215b and optionally to other elements of the flexible body harness 1200b. When the sets of pairs of straps 1220b, 1225b are mounted to a body segment and force is applied to one or both of the tethers, a corresponding set of pairs of straps 1220b, 1225b may be disposed along respective trajectories at least partially enclosing the body segment such that shear is evenly applied across the corresponding set(s) of straps 1220b, 1225b into skin of the body segment.

In another example, the locations at which such forces are applied, via respective tethers, may be substantially separate relative to the flexible body harness. This is illustrated by way of example in FIG. 12C, which illustrates an example flexible body harness 1200c. The flexible body harness 1200c includes first 1210c and second 1215c tethers via which forces may be applied to the flexible body harness 1200c. Due to the location of the tethers 1210c, 1215c, such forces may be applied to the flexible body harness 1200c at locations that are substantially separate. Two sets of pairs of straps 1220c, 1225c are each coupled to a respective tether 1210c, 1215c and optionally to other elements of the flexible body harness 1200c. When the sets of pairs of straps 1220c, 1225c are mounted to a body segment and force is applied to one or both of the tethers, a corresponding set of pairs of straps 1220c, 1225c may be disposed along respective trajectories at least partially enclosing the body segment such that shear is evenly applied across the corresponding set(s) of straps 1220c, 1225c into skin of the body segment.

In yet another example, the forces may be applied in the same direction, at respective different locations, via respective tethers. This is illustrated by way of example in FIG. 12D, which illustrates an example flexible body harness 1200d. The flexible body harness 1200d includes first 1210d and second 1215d tethers via which forces may be applied to the flexible body harness 1200d. Due to the location of the tethers 1210d, 1215d, such forces may be applied to the flexible body harness 1200d at locations that are substantially separate and in the same direction relative to the body segment to which the flexible body harness 1200d is mounted. Two sets of pairs of straps 1220d, 1225d are each coupled to a respective tether 1210d, 1215d and optionally to other elements of the flexible body harness 1200d. When the sets of pairs of straps 1220d, 1225d are mounted to a body segment and force is applied to one or both of the tethers, a corresponding set of pairs of straps 1220d, 1225d may be disposed along respective trajectories at least partially enclosing the body segment such that shear is evenly applied across the corresponding set(s) of straps 1220d, 1225d into skin of the body segment.

Figure 12B:
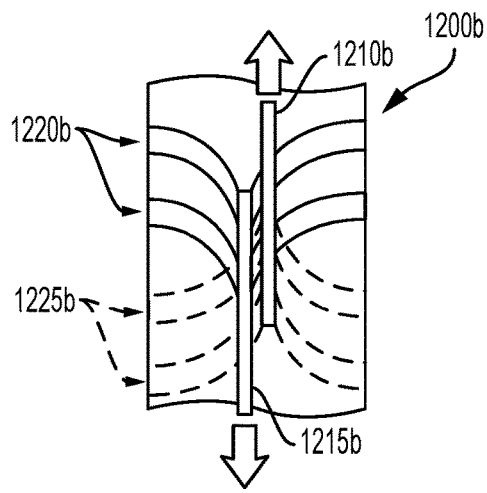
FIG. 12B is a schematic of elements of a body harness.
Figure 12C:
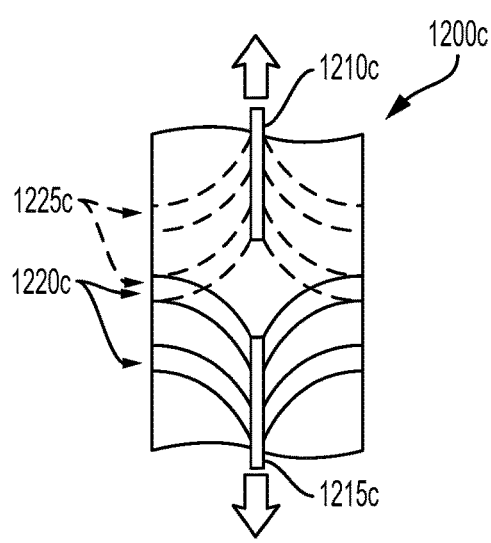
FIG. 12C is a schematic of elements of a body harness.
Figure 12D:
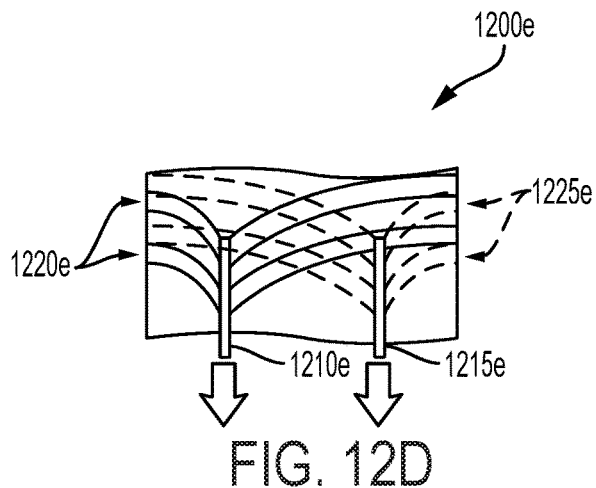
FIG. 12D is a schematic of elements of a body harness.
Figure 12E:
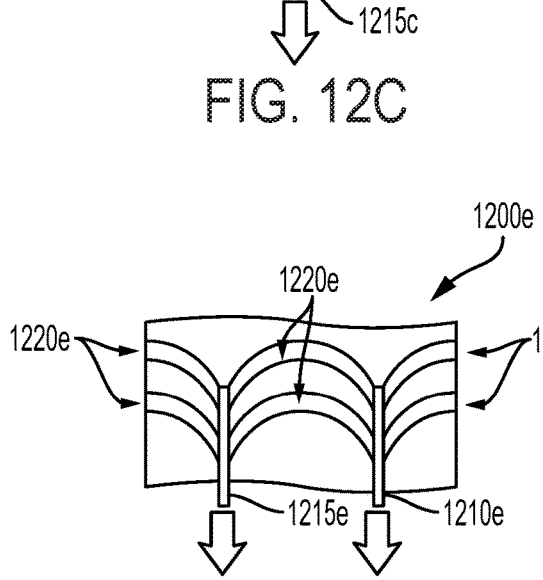
FIG. 12E is a schematic of elements of a body harness.

Note that, in the example flexible body harnesses 1200b, 1200c, and 1200d illustrated in FIGS. 12B, 12C, and 12D, respectively, each of the tethers of each of the flexible body harnesses is coupled to a respective disjoint set of straps. However, a flexible body harness as described herein may include straps that are each coupled to multiple tethers. This is illustrated by way of example in FIG. 12E, which illustrates an example flexible body harness 1200e. The flexible body harness 1200e includes first 1210e and second 1215e tethers via which forces may be applied to the flexible body harness 1200e. Due to the location of the tethers 1210e, 1215e, such forces may be applied to the flexible body harness 1200e at locations that are substantially separate and in directions that are oriented in the same direction relative to a body segment to which the flexible body harness 1200e is mounted. The flexible body harness 1200e includes a set of pairs of straps 1220e of which each strap is coupled to both of the first 1210e and second 1215e tethers and optionally to other elements of the flexible body harness 1200e. When the set of pairs of straps 1220e are mounted to a body segment and force is applied to both of the tethers, the set of pairs of straps 1220e may be disposed along trajectories at least partially enclosing the body segment such that shear is evenly applied across the set of pairs of straps 1220e into skin of the body segment.

Figure 12F:
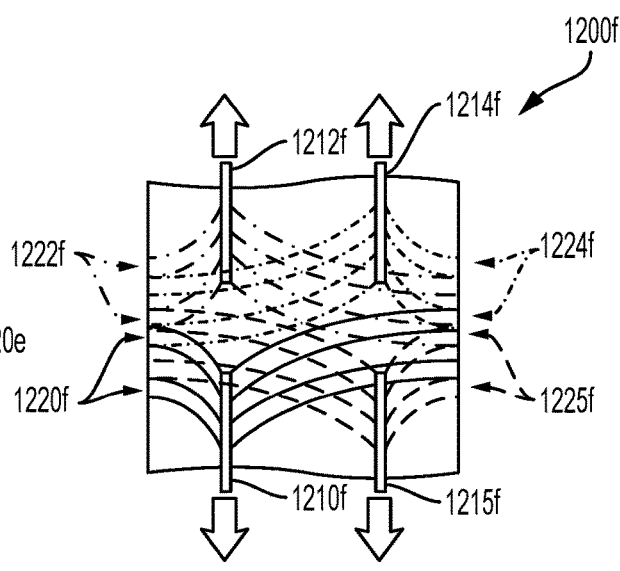
FIG. 12F is a schematic of elements of a body harness.

Further, flexible body harnesses as described herein may be configured to couple, in each of multiple directions, forces at multiple locations into skin of a segment of a body to which the flexible body harness is mounted. This is illustrated by way of example in FIG. 12F, which illustrates an example flexible body harness 1200f. The flexible body harness 1200f includes first 1210f and second 1215f tethers via which forces in a first direction may be applied to the flexible body harness 1200f. Due to the location of the tethers 1210f, 1215f, such forces may be applied to the flexible body harness 1200f at locations that are substantially separate relative to the body segment to which the flexible body harness 1200f is mounted. The flexible body harness 1200f also includes third 1212f and fourth 1214f tethers via which forces in a second direction that is different from the first direction may be applied to the flexible body harness 1200f. Due to the location of the tethers 1212f, 1214f, such forces may be applied to the flexible body harness 1200f at locations that are substantially separate relative to the body segment to which the flexible body harness 1200f is mounted. Four sets of pairs of straps 1220f, 1222f, 1224f, 1225f are each coupled to a respective tether 1210f, 1212f, 1214f, 1215f and optionally to other elements of the flexible body harness 1200f. When the sets of pairs of straps 1220f, 1222f, 1224f, 1225f are mounted to a body segment and force is applied to one or more of the tethers, a corresponding set of pairs of straps 1220f, 1222f, 1224f, 1225f may be disposed along respective trajectories at least partially enclosing the body segment such that shear is evenly applied across the corresponding set(s) of straps 1220f, 1222f, 1224f, 1225f into skin of the body segment.

The illustrated configurations of flexible body harnesses (e.g., 1200a, 1200b, 1200c, 1200d, 1200e, 1200f) and elements thereof (e.g., tethers, straps, flexible underlayers, load distributing elements) are intended as non-limiting example embodiments. Other configurations of such elements to form flexible body harnesses as described herein are anticipated by the inventors. Further, the illustrated configurations of straps and tethers of flexible body harnesses (e.g., as shown in FIGS. 12A, 12B, 12C, 12D, 12E, and 12F) could be applied to any of the varieties of flexible body harnesses as described herein, e.g., to body harnesses wherein straps of the harness are disposed on or within a flexible underlayer of the harnesses and/or to body harnesses wherein straps of the harness are woven together and/or woven with alignment straps.

IV. Conclusion

Embodiments described herein are intended as illustrative, non-limited examples of body harnesses that can be used to apply forces or loads to segments of a body. Such body harnesses could be configured to apply loads to one or more segments of a body according to a variety of applications. For example, body harnesses as described herein could be applied as part of an exosuit or other prosthetic device or system configured to apply assistive forces to segments of a human body via such body harnesses, e.g., to increase the strength or endurance of the human body, to assist with rehabilitation, to improve coordination of the human body, or to provide some other functionality. Such forces could be transmitted, via such body harnesses, between different segments of the body (e.g., between a calf and a thigh, to assist and/or resist knee motion or torque), between segments of the body and prosthetic devices (e.g., between a thigh and a lower-limb prosthesis), between segments of the body and other objects (e.g., to provide means for distributing the weight of a pack or other load across skin of a body segment), or forces could be transmitted, using such body harnesses, in some other way. A body harness may be configured to apply forces to the lower body, upper body, torso, or combinations of some or all of these parts of a wearer or other body segments.

Dimensions, configurations, or other properties of a body harness as described herein could be configured to be used by a variety of users (e.g., a one-size-fits-all brace, a body harness including adjustable straps, buttons, hook-and-loop materials, fasteners, or other means to adjust a dimension or other property to a wearer) or could be custom-tailored or otherwise manufactured specifically for an individual user. Some elements of a body harness could have a single size and/or configuration for a variety of users (e.g., lengths and/or trajectories of force-transmitting straps), while other elements (e.g., undersuits, rigid force-transmitting elements, flexible force-transmitting elements) could be chosen from sets of elements having a range of sizes such that the chosen elements had a size matched to the wearer. 3D printing, rapid prototyping, tailoring, or other methods of customized fabrication could be used to produce elements of a body harness specifically configured to be worn and/or used by a specific wearer.

Body harnesses as described herein could be configured for use by anatomically typical human wearers or by atypical human wearers. Body harnesses could be configured to be worn and operated by human wearers that have lost parts of their body (e.g., arms, legs), that have experienced some alteration of anatomy due to surgical intervention (e.g., tendon transfer) or that are anatomically atypical.

Body harnesses as described herein could be configured for use by non-human animals. For example, a body harness could be configured to be worn by a non-human primate, a dog, a horse, or some other animal according to an application, e.g., animal training.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A flexible body harness, wherein the flexible body harness is mountable to a segment of a body such that the flexible body harness is configured to at least partially enclose the segment of the body, and wherein the flexible body harness comprises:

a flexible underlayer;
   a tether, wherein the tether is configured to extend along a length of the segment of the body when the flexible body harness is mounted to the segment of the body; and
   first and second straps, wherein the first and second straps are coupled to the tether and to the flexible underlayer such that, when the flexible body harness is mounted to the segment of the body such that the flexible body harness is configured to at least partially enclose the segment of the body, the first and second straps are disposed along respective first and second trajectories at least partially around the segment of the body, wherein a portion of the first trajectory corresponds to a section of a catenary curve, wherein the first and second trajectories configured to be around the segment of the body are on respective sides of the flexible body harness relative to the tether, wherein respective angles of the first trajectory and second trajectory relative to the tether are less than 90 degrees and increase with distance along the first strap and second strap, respectively, from the tether across at least a respective portion of each of the first strap and the second strap such that, when a force is applied to the flexible body harness via the tether, a shear is configured to be applied to skin of the segment of the body, via the first and second straps and the underlayer, that is substantially even across the respective portions of each of the first and second straps.

2. The flexible body harness of claim 1, wherein the first and second straps are disposed on the flexible underlayer.

3. The flexible body harness of claim 2, wherein a coupling location between the flexible underlayer and the first strap is adjustable such that the first trajectory can be adjusted.

4. The flexible body harness of claim 3, wherein the flexible underlayer and the first strap are coupled by a layer of hook-and-loop fasteners.

5. The flexible body harness of claim 2, wherein the flexible underlayer and the first strap are coupled such that a strength of coupling between the first strap and the flexible underlayer at a particular location along the first strap decreases when a shear between the first strap and the flexible underlayer at the particular location increases beyond a specified maximum shear.

6. The flexible body harness of claim 2, wherein the first strap comprises a plurality of projections that are configured to distribute the shear applied to the skin of the segment of the body from the first strap via the flexible underlayer when the flexible body harness is mounted to the segment of the body and the force is applied to the flexible body harness via the tether.

7. The flexible body harness of claim 2, wherein the flexible underlayer is more flexible, at a particular location along the first strap, in a direction of the first strap at the particular location than in a direction perpendicular to the direction of the first strap at the particular location.

8. The flexible body harness of claim 2, wherein the first and second trajectories overlap at a location on the flexible underlayer that is configured to be on an opposite side of the segment of the body from the tether and wherein the first and second straps are coupled together at an intersection of the first and second trajectories.

9. The flexible body harness of claim 2, wherein the first and second straps form a single continuous strap that is configured to at least partially enclose the segment of the body when the flexible body harness is mounted to the segment of the body.

10. The flexible body harness of claim 1, wherein the first and second straps are formed within the flexible underlayer.

11. The flexible body harness of claim 1, further comprising:

a further tether; and
   third and fourth straps, wherein the third and fourth straps are coupled to the further tether and to the flexible underlayer such that, when the flexible body harness is mounted to the segment of the body such that the flexible body harness is configured to at least partially enclose the segment of the body, the third and fourth straps are disposed along respective third and fourth trajectories at least partially around the segment of the body, wherein the third and fourth trajectories configured to be at least partially around the segment of the body are on respective sides of the flexible body harness relative to the further tether, wherein respective angles of the third trajectory and fourth trajectory relative to the further tether increase with distance along the third strap and fourth strap, respectively, from the further tether across at least a respective portion of each of the third strap and the fourth strap such that, when a force is applied to the flexible body harness via the further tether, a shear is configured to be applied to the skin of the segment of the body, via the third and fourth straps and the underlayer, that is substantially even across the respective portions of each of the third and fourth straps.

12. The flexible body harness of claim 1, further comprising:
   third and fourth straps, wherein the third and fourth straps are coupled to the tether and to the flexible underlayer such that, when the flexible body harness is mounted to the segment of the body such that the flexible body harness is configured to at least partially enclose the segment of the body, the third and fourth straps are disposed along respective third and fourth trajectories at least partially around the segment of the body, wherein the third and fourth trajectories configured to be at least partially around the segment of the body are on respective sides of the flexible body harness relative to the tether, wherein respective angles of the third trajectory and fourth trajectory relative to the tether increase with distance along the third strap and fourth strap, respectively, from the tether across at least a respective portion of each of the third strap and the fourth strap such that, when the force is applied to the flexible body harness via the tether, a shear is configured to be applied to the skin of the segment of the body, via the third and fourth straps and the underlayer, that is substantially even across the respective portions of each of the third and fourth straps; and
   a load distributor, wherein the first, second, third, and fourth straps are coupled to the tether via the load distributor, wherein the load distributor comprises:
   a first pulley that is coupled to the tether;
   a second pulley that is coupled to the first and second straps;
   a third pulley that is coupled to the third and fourth straps; and
   a continuous loop of load-bearing material, wherein the continuous loop of load-bearing material is threaded between the first, second, and third pulleys such that, when the force is applied to the flexible body harness via the tether, a ratio between a force applied from the tether to the first and second straps and a force applied from the tether to the third and fourth straps corresponds to a specified ratio.

13. The flexible body harness of claim 1, wherein respective angles of the first trajectory and second trajectory relative to the tether increase with distance along the first strap and second strap, respectively, from the tether across the respective portions of each of the first and second straps such that, when the force is applied to the flexible body harness via the tether, the shear is configured to be applied to the skin of the segment of the body, via the first and second straps and the underlayer, that varies across the respective portions of each of the first strap and the second strap by less than 10%.

14. A flexible body harness, wherein the flexible body harness is mountable to a segment of a body such that the flexible body harness is configured to at least partially enclose the segment of the body, and wherein the flexible body harness comprises:
   a tether, wherein the tether is configured to extend along a length of the segment of the body when the flexible body harness is mounted to the segment of the body; and
   first and second straps, wherein the first and second straps are coupled to the tether such that, when the flexible body harness is mounted to the segment of the body such that the flexible body harness is configured to at least partially enclose the segment of the body, the first and second straps are disposed along respective first and second trajectories at least partially around the segment of the body, wherein a portion of the first trajectory corresponds to a section of a catenary curve, wherein the first and second trajectories configured to be around the segment of the body are on respective sides of the flexible body harness relative to the tether, wherein respective angles of the first trajectory and second trajectory relative to the tether are less than 90 degrees and increase with distance along the first strap and second strap, respectively, from the tether across at least a respective portion of each of the first strap and the second strap such that, when a force is applied to the flexible body harness via the tether, a shear is configured to be applied to skin of the segment of the body, via the first and second straps, that is substantially even across respective portions of each of the first and second straps; and
   a plurality of alignment straps, wherein the plurality of alignment straps are woven together with the first and second straps to maintain the first and second straps along the first and second trajectories, respectively, when the force is applied to the flexible body harness via the tether.

15. The flexible body harness of claim 14, further comprising:
   third and fourth straps, wherein the third and fourth straps are coupled to the tether such that, when the flexible body harness is mounted to the segment of the body such that the flexible body harness is configured to at least partially enclose the segment of the body, the third and fourth straps are disposed along respective third and fourth trajectories at least partially around the segment of the body, wherein the third and fourth trajectories configured to be around the segment of the body are on respective sides of the flexible body harness relative to the tether, wherein respective angles of the third trajectory and fourth trajectory relative to the tether increase with distance along the third strap and fourth straps, respectively, from the tether across at least a respective portion of each of the third strap and the fourth strap such that, when the force is applied to the flexible body harness via the tether, a shear is configured to be applied to the skin of the segment of the body, via the third and fourth straps and an underlayer, that is substantially even across the respective portions of each of the third and fourth straps, and wherein the plurality of alignment straps are woven together with the third and fourth straps to maintain the third and fourth straps along the third and fourth trajectories, respectively, when the force is applied to the flexible body harness via the tether.

16. The flexible body harness of claim 14, further comprising:
   a further tether; and
   third and fourth straps, wherein the third and fourth straps are coupled to the further tether such that, when the flexible body harness is mounted to the segment of the body such that the flexible body harness is configured to at least partially enclose the segment of the body, the third and fourth straps are disposed along respective third and fourth trajectories at least partially around the segment of the body, wherein the third and fourth trajectories configured to be at least partially around the segment of the body are on respective sides of the flexible body harness relative to the further tether, wherein respective angles of the third trajectory and fourth trajectory relative to the further tether increase with distance along the third strap and fourth strap, respectively, from the further tether across at least a respective portion of each of the third strap and the fourth strap such that, when a force is applied to the flexible body harness via the further tether, a shear is configured to be applied to the skin of the segment of the body, via the third and fourth straps, that is substantially even across the respective portions of each of the third and fourth straps, and wherein the plurality of alignment straps are woven together with the third and fourth straps to maintain the third and fourth straps along the third and fourth trajectories, respectively, when the force is applied to the flexible body harness via the further tether.

17. The flexible body harness of claim 14, wherein respective angles of the first trajectory and second trajectory relative to the tether increase with distance along the first strap and second strap, respectively, from the tether across the respective portions of each of the first and second straps such that, when the force is applied to the flexible body harness via the tether, the shear is configured to be applied to the skin of the segment of the body, via the first and second straps, that varies across the respective portions of each of the first strap and the second strap by less than 10%.

* * * * *